(12) United States Patent
Cho et al.

(10) Patent No.: US 8,974,497 B2
(45) Date of Patent: Mar. 10, 2015

(54) VERTEBRAL SUPPORT DEVICE

(75) Inventors: Paul Cho, Colleyville, TX (US); Reginald Davis, Cockeysville, MD (US); Gregory Hoffman, Fort Wayne, IN (US); Alan McGee, Fort Wayne, IN (US); John Williams, Fort Wayne, IN (US); Arnold M. Schwartz, Huntington Bay, NY (US); William D. Bradley, Frisco, TX (US); Alexandre Jodaitis, Morlanwelz (BE); Herve Chataigner, Bussieres (FR); Hugo Santos Benitez, Madrid (ES); Chen Zhongqiang, Beijing (CN)

(73) Assignee: LDR Medical, Rosières Près Troyes (FR)

( * ) Notice: Subject to any disclaimer, the term of this patent is extended or adjusted under 35 U.S.C. 154(b) by 1371 days.

(21) Appl. No.: 11/958,285

(22) Filed: Dec. 17, 2007

(65) Prior Publication Data

US 2008/0255617 A1 Oct. 16, 2008

(30) Foreign Application Priority Data

Dec. 21, 2006 (FR) ...................... 06 11198

(51) Int. Cl.
*A61B 17/70* (2006.01)
(52) U.S. Cl.
CPC ........... *A61B 17/7034* (2013.01); *A61B 17/702* (2013.01); *A61B 17/7031* (2013.01); *A61B 17/7041* (2013.01); *A61B 17/705* (2013.01)
USPC ............................. 606/255; 606/259; 606/254
(58) Field of Classification Search
USPC ................... 606/246–259, 260–278
See application file for complete search history.

(56) References Cited

U.S. PATENT DOCUMENTS

| 4,743,260 A | 5/1988 | Burton |
| 5,437,669 A | 8/1995 | Yuan et al. |

(Continued)

FOREIGN PATENT DOCUMENTS

| DE | 10348329 | 2/2005 |
| EP | 0381588 | 8/1990 |

(Continued)

OTHER PUBLICATIONS

World Intellectual Property Organization; International Preliminary Report on Patentability for International Application No. PCT/IB2007/004061; Jan. 15, 2009; WIPO; Geneva, Switzerland; all pages.

(Continued)

*Primary Examiner* — Jan Christopher Merene
(74) *Attorney, Agent, or Firm* — Denko Coburn Lauff LLP

(57) ABSTRACT

A vertebral support device (1) is disclosed, which in various embodiments comprises at least two osseous anchoring implants (2), each designed to be anchored to a vertebra, and at least one linking element (3) fixed to the osseous anchoring implants (2) by fasteners (20) that maintain a fixed angle between the longitudinal axis (L) of the linking element (3) passing through rigid elements (34) of the linking element (3) and the insertion axis (DV) of the implants (2). The linking element (3) includes at least one elastic dampening element (31) that that allows the implant-bearing vertebrae some freedom of movement. The dampening element (31) accommodates the stresses imposed on the linking element (3) during movement of the vertebrae and tends to return the support device (1) to its normal configuration.

13 Claims, 21 Drawing Sheets

(56) References Cited

U.S. PATENT DOCUMENTS

| | | | |
|---|---|---|---|
| 5,501,684 A | 3/1996 | Schlaepfer et al. | |
| 5,520,689 A | 5/1996 | Schlaepfer et al. | |
| 5,540,688 A | 7/1996 | Navas | |
| 5,603,714 A | 2/1997 | Kaneda et al. | |
| 5,672,175 A | 9/1997 | Martin | |
| 6,267,764 B1 | 7/2001 | Elberg | |
| 6,447,546 B1 | 9/2002 | Bramlet et al. | |
| 6,626,904 B1 | 9/2003 | Jammet et al. | |
| 6,770,075 B2 | 8/2004 | Howland | |
| 6,783,527 B2 | 8/2004 | Drewry et al. | |
| 6,966,910 B2 | 11/2005 | Ritland | |
| 7,037,340 B2 | 5/2006 | Gau | |
| 7,056,344 B2 | 6/2006 | Huppert et al. | |
| 7,083,622 B2 | 8/2006 | Simonson | |
| 7,160,300 B2 | 1/2007 | Jackson | |
| 7,291,170 B2 | 11/2007 | Huppert | |
| 7,326,250 B2 | 2/2008 | Beaurain et al. | |
| 7,329,258 B2 * | 2/2008 | Studer | 606/250 |
| 7,361,196 B2 | 4/2008 | Fallin et al. | |
| 7,494,508 B2 | 2/2009 | Zeegers | |
| 7,507,248 B2 | 3/2009 | Beaurain et al. | |
| 7,594,931 B2 | 9/2009 | Louis et al. | |
| 7,604,654 B2 | 10/2009 | Fallin et al. | |
| 7,621,912 B2 | 11/2009 | Harms et al. | |
| 7,621,940 B2 | 11/2009 | Harms et al. | |
| 7,625,393 B2 | 12/2009 | Fallin et al. | |
| 7,632,282 B2 | 12/2009 | Dinville | |
| 7,682,396 B2 | 3/2010 | Beaurain et al. | |
| 7,695,516 B2 | 4/2010 | Zeegers | |
| 7,695,518 B2 | 4/2010 | Gau | |
| 7,744,630 B2 | 6/2010 | Lancial | |
| 7,744,634 B2 | 6/2010 | Farris | |
| 7,842,088 B2 | 11/2010 | Rashbaum et al. | |
| 7,854,752 B2 | 12/2010 | Colleran et al. | |
| 8,002,835 B2 | 8/2011 | Zeegers | |
| 8,147,556 B2 | 4/2012 | Louis et al. | |
| 8,162,988 B2 | 4/2012 | Delecrin et al. | |
| 8,202,301 B2 | 6/2012 | Prevost et al. | |
| 8,221,422 B2 | 7/2012 | Mangione | |
| 8,221,457 B2 | 7/2012 | Delecrin et al. | |
| 8,241,359 B2 | 8/2012 | Davis et al. | |
| 8,246,657 B1 | 8/2012 | Samuel | |
| 8,257,439 B2 | 9/2012 | Zeegers | |
| 8,262,700 B2 | 9/2012 | Cho et al. | |
| 8,267,999 B2 | 9/2012 | Beaurain et al. | |
| 8,343,219 B2 | 1/2013 | Allain et al. | |
| 8,409,288 B2 | 4/2013 | Davis et al. | |
| 8,430,915 B2 | 4/2013 | Beaurain et al. | |
| 8,439,931 B2 | 5/2013 | Dinville | |
| 8,465,526 B2 | 6/2013 | Friedrich et al. | |
| 8,465,546 B2 | 6/2013 | Jodaitis et al. | |
| 8,491,637 B2 | 7/2013 | Matthis et al. | |
| 8,623,087 B2 | 1/2014 | Huppert | |
| 8,632,591 B2 | 1/2014 | Vila et al. | |
| 8,685,100 B2 | 4/2014 | Jodaitis et al. | |
| 8,696,709 B2 | 4/2014 | Dinville et al. | |
| 8,753,397 B2 | 6/2014 | Beaurain et al. | |
| 8,771,284 B2 | 7/2014 | Rashbaum et al. | |
| 8,845,691 B2 | 9/2014 | Renaud et al. | |
| 2002/0160891 A1* | 10/2002 | Gallagher | 482/123 |
| 2003/0191470 A1 | 10/2003 | Ritland | |
| 2004/0172020 A1* | 9/2004 | Beaurain et al. | 606/61 |
| 2005/0065514 A1* | 3/2005 | Studer | 606/61 |
| 2005/0065516 A1 | 3/2005 | Jahng | |
| 2005/0085815 A1* | 4/2005 | Harms et al. | 606/61 |
| 2005/0101956 A1 | 5/2005 | Simonson | |
| 2005/0171543 A1* | 8/2005 | Timm et al. | 606/61 |
| 2005/0177157 A1 | 8/2005 | Jahng | |
| 2005/0192570 A1 | 9/2005 | Jackson | |
| 2005/0203519 A1* | 9/2005 | Harms et al. | 606/61 |
| 2005/0277922 A1* | 12/2005 | Trieu et al. | 606/61 |
| 2005/0277926 A1* | 12/2005 | Farris | 606/61 |
| 2006/0036240 A1* | 2/2006 | Colleran et al. | 606/61 |
| 2006/0111712 A1 | 5/2006 | Jackson | |
| 2006/0111715 A1 | 5/2006 | Jackson | |
| 2006/0142760 A1 | 6/2006 | McDonnell | |
| 2006/0189984 A1* | 8/2006 | Fallin et al. | 606/61 |
| 2006/0264937 A1* | 11/2006 | White | 606/61 |
| 2007/0049937 A1* | 3/2007 | Matthis et al. | 606/61 |
| 2007/0112428 A1* | 5/2007 | Lancial | 623/17.12 |
| 2007/0270838 A1* | 11/2007 | Bruneau et al. | 606/61 |
| 2009/0005817 A1* | 1/2009 | Friedrich et al. | 606/246 |
| 2010/0010543 A1 | 1/2010 | Jackson | |
| 2010/0063545 A1 | 3/2010 | Richelsoph | |
| 2010/0087863 A1 | 4/2010 | Biedermann et al. | |
| 2010/0274288 A1* | 10/2010 | Prevost et al. | 606/257 |
| 2011/0184412 A1 | 7/2011 | Scifert et al. | |

FOREIGN PATENT DOCUMENTS

| | | |
|---|---|---|
| EP | 0516567 | 12/1992 |
| EP | 0669109 | 8/1995 |
| JP | 2005511974 | 4/2005 |
| JP | 2005118569 | 5/2005 |
| JP | 2008502448 | 1/2008 |
| JP | 4299669 | 7/2009 |
| JP | 4465251 | 5/2010 |
| WO | WO9116018 | 10/1991 |
| WO | WO9822033 | 5/1998 |
| WO | WO03037216 | 5/2003 |
| WO | WO03047442 | 6/2003 |
| WO | WO2004089244 | 10/2004 |
| WO | WO2005030031 | 4/2005 |
| WO | WO2005092218 | 10/2005 |
| WO | WO2006057813 | 6/2006 |
| WO | WO2006057837 | 6/2006 |
| WO | WO2006119447 | 11/2006 |
| WO | WO2010074695 | 7/2010 |

OTHER PUBLICATIONS

World Intellectual Property Organization; International Search Report and Written Opinion of the International Searching Authority for International Application No. PCT/IB2007/004061; Sep. 18, 2008; WIPO; Geneva, Switzerland; all pages.

Implant for Osseous Anchoring with Polyaxial Head, U.S. Appl. No. 10/498,234, filed Dec. 7, 2004.

Intervertebral Disc Prosthesis and Instrumentation for Insertion of the Prosthesis Between the Vertebrae, U.S. Appl. No. 11/362,253, filed Feb. 24, 2006.

Vertebral Support Device, U.S. Appl. No. 11/958,285, filed Dec. 17, 2007.

Intervertebral disc prosthesis, surgical methods, and fitting tools, U.S. Appl. No. 12/025,677, filed Feb. 4, 2008.

Intervertebral Disc Prosthesis, U.S. Appl. No. 12/955,898, filed Nov. 29, 2010.

Instruments and Methods for Removing Fixation Devices from Intervertebral Implants, U.S. Appl. No. 13/158,761, filed Jun. 13, 2011.

Intervertebral Disc Prosthesis, U.S. Appl. No. 13/215,123, filed Aug. 22, 2011.

Vertebral Cage Device With Modular Fixation, U.S. Appl. No. 13/438,352, filed Apr. 3, 2012.

Plate for osteosynthesis device and method of preassembling such device, U.S. Appl. No. 13/454,927, filed Apr. 24, 2012.

Anchoring Device and System for an Intervertebral Implant, Intervertebral Implant and Implantation Instrument, U.S. Appl. No. 13/520,041, filed Jun. 29, 2012.

Anchoring Device and System for an Intervertebral Implant, Intervertebral Implant and Implantation Instrument, U.S. Appl. No. 13/538,078, filed Jun. 29, 2012.

Transforaminal intersomatic cage for an intervertebral fusion graft and an instrument for implanting the cage, U.S. Appl. No. 13/585,063, filed Aug. 14, 2012.

Intervertebral Disc Prosthesis, U.S. Appl. No. 13/603,043, filed Sep. 4, 2012.

Intersomatic cage, intervertebral prosthesis, anchoring device and implantation instruments, U.S. Appl. No. 13/732,244, filed Dec. 31, 2012.

(56) References Cited

OTHER PUBLICATIONS

Anchoring device and system for an intervertebral implant, intervertebral implant and implantation instrument, U.S. Appl. No. 13/774,547, filed Feb. 22, 2013.
Transforanimal intersomatic cage for an intervertebral fusion graft and an instrument for implanting the cage, U.S. Appl. No. 13/854,808, filed Apr. 1, 2013.
Spinal Osteosynthesis Device and Preparation Method, U.S. Appl. No. 13/873,190, filed Apr. 29, 2013.
Instrumentation and Methods for Inserting an Intervertebral Disc Prosthesis, U.S. Appl. No. 13/892,933, filed May 13, 2013.
Intervertebral disc prosthesis insertion assemblies, U.S. Appl. No. 13/919,704, filed Jun. 17, 2013.
Interspinous Implant and Implantation Instrument, U.S. Appl. No. 14/130,286, filed Dec. 31, 2013.
Intersomatic cage with unified grafts, U.S. Appl. No. 14/149,357, filed Jan. 7, 2014.
Nucleus Prostheses, U.S. Appl. No. 14/159,161, filed Jan. 20, 2014.
Intervertebral disc prosthesis insertion assemblies, U.S. Appl. No. 14/242,177, filed Apr. 1, 2014.
Vertebral implant, vertebral fastening device of the implant and implant instrumentation, U.S. Appl. No. 14/246,442, filed Apr. 7, 2014.
Interspinous Implant and Implantation Instrument, U.S. Appl. No. 14/252,754, filed Apr. 14, 2014.
Anchoring device for a spinal implant, spinal implant and implantation instrumentation, U.S. Appl. No. 14/252,852, filed Apr. 15, 2014.
Intervertebral Disk Prosthesis, U.S. Appl. No. 14/306,785, filed Jun. 17, 2014.
Intervertebral Disc Prosthesis and Instrumentation for Insertion of the Prosthesis Between the Vertebrae, U.S. Appl. No. 14/325,317, filed Jul. 7, 2014.
Anchoring device and system for an intervertebral implant, intervertebral implant and implantation instrument, U.S. Appl. No. 14/380,714, filed Aug. 23, 2014.
Osseous anchoring implant with a polyaxial head and method for installing the implant, U.S. Appl. No. 14/497,321, filed Sep. 26, 2014.

National Institute of Industrial Property (France); Search Report in Fench Pub. No. FR2910267; Dec. 18, 2007; National Institute of Industrial Property (France); France; all pages.
World Intellectual Property Organization; International Preliminary Report on Patentability for PCT Pub'n No. WO 2008/078163; Jan. 15, 2009; WIPO; Geneva, Switzerland; all pages.
World Intellectual Property Organization; Written Opinion of the International Searching Authority for PCT Pub'n No. WO 2008/078163; Sep. 18, 2008; WIPO; Geneva, Switzerland; all pages.
World Intellectual Property Organization; International Search Report for PCT Pub'n No. WO 2008/078163; Sep. 18, 2008; WIPO; Geneva, Switzerland; all pages.
Zimmer Spine; Dynesys® Dynamic Stabilization System: A Guide for Patients; Jul. 21, 2005; Zimmer Spine; USA; all pages.
R. Eberlein; FEA of a Spinal Implant, Human Intervertebral Discs and the Human Lumbar Spine—Relevance for the Business Process; Jun. 12, 2002; Sulzer Innotec; Vienna, Austria; all pages.
University of Pittsburg; Dynesys® Spine Stabilization System; accessed Oct. 2, 2006; University of Pittsburg; Internet; all pages.
Zimmer Spine; Dynesys® Dynamic Stabilization System; Jul. 21, 2005; Zimmer Spine; Internet; all pages.
Thomas M. Stoll, et al.; The dynamic neutralization system for the spine: a multi-center study of a novel non-fusion system; Sep. 10, 2002; European Spine Journal; Internet; all pages.
Burtonreport.com; The Concept of "Flexible Stabilization" (Dynamic Spine Stabilization); accessed Oct. 2, 2006; Internet; all pages.
Kevin T. Foley, et al.; Design and Testing of a Novel Posterior Dynamic Stabilization Device; Jul. 12-15, 2006; IMAST; Athens, Greece; all pages.
U.S. Food and Drug Administration; 510(k) 031511; Mar. 5, 2004; U.S. Food and Drug Administration; USA; all pages.
U.S. Food and Drug Administration; 510(k) 043565; Mar. 11, 2005; U.S. Food and Drug Administration; USA; all pages.
U.S. Food and Drug Administration; 510(k) 060638; Apr. 6, 2006; U.S. Food and Drug Administration; USA; all pages.

* cited by examiner

VERTEBRAL SUPPORT DEVICE

RELATED APPLICATIONS

This application claims priority under 35 U.S.C. §119 to French Patent Application No. 06 11198, filed in FRANCE on Dec. 21, 2006.

TECHNICAL FIELD

This present invention concerns intervertebral devices and prostheses that can be implanted onto the spinal column, and more particularly a vertebral support device.

BACKGROUND

It would be advantageous to have a vertebral support device that supports the vertebrae on which it is implanted, while still offering a certain freedom of movement of the vertebrae and, as a consequence, preventing the fusion of these vertebrae, unlike various known osteosynthesis devices.

Various types of osteosynthesis devices are discussed, for example, in patent applications WO02/080788 and WO95/10240 and in U.S. Pat. No. 5,603,714, and U.S. Pat. No. 5,437,669. These devices include at least two bone-anchoring implants, each designed to be anchored to a vertebra and connected together by a linking element (an osteosynthesis bar), using fasteners such as clamps to securely attach the bone-anchoring implants and the linking element. By immobilizing the vertebrae on which it is implanted, this type of device is used to achieve intervertebral fusion, to reduce spondylolisthesis or to correct scolioses or other defects of the spinal column. Also, patent applications WO03/049629, EP 0572790, WO 2005/020829, and WO 00/15125, and U.S. Pat. No. 5,501,684 discuss various types of vertebral anchoring implants facilitating, to varying degrees, the fitting of elements of the osteosynthesis device, the reduction of spondylolisthesis, or the correction of defects of the spinal column. However, these devices provide no freedom of movement of the vertebrae and lead to a fusion of the vertebrae on which they are implanted, which has the disadvantage for the patient of limiting movement and of transferring the stresses normally experienced by these vertebrae onto the adjacent vertebrae and onto the adjacent intervertebral discs. Patent applications WO02/080788, WO03/049629, and WO 2005/020829 are assigned to the assignee of the present application, and are incorporated by reference herein for all purposes.

Other references discuss vertebral support devices comprising osseous anchorage implants linked together by a flexible linking element. For example, U.S. Pat. No. 5,672,175, U.S. Pat. No. 4,743,260, and U.S. Pat. No. 7,083,622 discuss vertebral support devices having implants that are linked together by a flexible bar. These devices allow only a lateral movement, thereby accommodating stresses occurring laterally with respect to the axis of the spinal column but not in the direction of flexion or extension of the spinal column. Patent applications WO 91/16018 (corresponding to patent EP 0 381 588 B1), WO 2004/089244 (corresponding to U.S. Pat. No. 6,966,910 B2) and WO 03/037216 (corresponding to U.S. Pat. No. 6,783,527 B2) discuss vertebral support devices in which the linking element between the implants generally comprise an elastic ligament maintaining a permanent tension between the implants. This type of elastic ligament, used alone, tends to bring the implants together along with the vertebrae on which they are attached, and does not provide an adjustable orientation of the linking element with respect to the implants or of the position of the articulation. Patent applications WO 98/22033 (corresponding to U.S. Pat. No. 6,267,764 B1) and WO 2005/030031 discuss support devices that comprise an elastic ligament fixed to bars linked to the implants, which allows a measure of positioning of the articulation between the implants, but these devices do not necessarily allow an adjustment of the orientation of the bars, and these devices do not provide a central portion absorbing the stresses in compression occurring between the implants. Patent EP 0 669 109 B1, for example, discusses a support device comprising an elastic ligament surrounded by an elastic central portion absorbing the stresses in compression between the implants, and patent application WO 2005/092218 discusses a device comprising an elastic ligament inserted in rigid spacers fitting together and forming a string with the ligament. In these devices, however, the implants rest directly on the central portion or the rigid spacers, which does not permit adjustment of the orientation or the position of the articulation between the implants. U.S. Pat. No. 5,540,688 (corresponding to patent EP 0 516 567 B1) discusses a device comprising an elastic ligament surrounded by a central dampening portion and, in some embodiments, by additional surrounding elements. The position of the ligament with respect to the implants cannot be adjusted, nor can the point of articulation.

SUMMARY

In this context, the present invention provides various embodiments having various features and combinations of features addressing some of the disadvantages of other designs. For example, a vertebral support device is provided that can be used to maintain (or restore) the distance (along the axis of the spinal column) between the vertebrae on which it is implanted (maintain or restore a height between the vertebrae), while preventing the arthrodesis (definitive immobilization and intervertebral fusion) of some or all of such vertebrae. Various embodiments of the support device provide flexible articulation that allows some freedom of movement of these vertebrae, which can relieve the intervertebral disc by absorbing part of the stresses that can damage the disc. In some embodiments, correction of defects of the spinal column can be accomplished by maintaining a permanent tension between the vertebrae, which limits separation of the vertebrae while allowing adjustment of the position of articulation between the implants and adjustment of the orientation of the support device with respect to the spinal column.

Various embodiments of the present invention provide selected features with a vertebral support device (1) comprising at least two osseous anchoring implants (2), each designed to be anchored to a vertebra along an insertion axis (DV) and at least one linking element (3) connecting the osseous anchoring implants (2) and having a longitudinal axis (L). The linking element (3) comprises rigid elements (34) and a dampening element (31) having a central elastic portion (32) and a longitudinal elastic portion (33), with the rigid elements (34) articulated by the dampening element (31).

The articulation of the rigid elements (34) provides freedom of movement to the vertebrae on which the device (1) is attached. In various embodiments, the dampening element (31) accommodates the stresses experienced by the linking element (3) during these movements, and tends to return the device (1) to its normal configuration. In various embodiments, the central elastic portion (32) of the dampening element (31) cooperates with rigid element (34) to accommodate the compression stresses occurring on the linking element (3), and the longitudinal elastic portion (33) accommodates the extension or flexion stresses occurring on the linking element (3). For many applications of the various embodiments described in this disclosure, each implant (2) is anchored to the pedicles of a vertebra along an axis called a dorso-ventral (DV) axis. Accordingly, the insertion axis along which an implant (2) is anchored to a vertebra will be referred to herein as a "dorso-ventral axis (DV)," which nomenclature, as discussed further below, is adopted solely for convenience of description. Thus, a reference in this specification to a "dorso-ventral axis (DV)" shall be a reference to any axis of insertion for an insert, and shall not limit the insertion axis to any particular place or any particular orientation. In addition, this specification uses the nomenclature "longitudinal axis" as a general and nonlimiting reference to a direction in which an elongated object is elongated, as more fully discussed below.

In selected embodiments, a fastener (20) fixes each rigid element (34) to an implant (2) so that after the fastener is tightened the longitudinal axis (L) of the linking element (3) extending through the rigid element (34) and the insertion axis (DV) of the implant (2) establish a fixed angle.

In selected embodiments, the longitudinal elastic portion (33) comprises ends, each fixed with respect to the implants (2) and/or to the rigid elements (34) by fasteners (330, 331).

In selected embodiments, the central portion (32) of the dampening element (31) is located substantially equally distant from each of the implants (2) between which it is located, on the longitudinal axis (L) of the linking element (3).

In selected embodiments, the position of the central portion (32) of the dampening element (31) between the implants (2) is off-centre in the longitudinal axis (L) of the linking element (3).

In selected embodiments, the dampening element (31) is composed of at least one elastic material.

In selected embodiments, the dampening element (31) comprises at least one elastic weave or braid of synthetic fibers, with the stitches of this weave or the plaits of this braid being tightened to varying degrees, to adjust the elastic properties of the dampening element (31) according to the desired elasticity.

In selected embodiments, the central portion (32) of the dampening element (31) has an outside diameter that is, to varying degrees, larger than the outside diameter of the tubes (34) of the linking element (3).

In selected embodiments, the tension of the elastic longitudinal portion (33) can be adjusted with the fasteners (330, 331).

In selected embodiments, the elastic longitudinal portion (33) includes, at least close to at least one of its ends, at least one tension mark that can be used to identify at least one position at which the fasteners (330, 331) must block the longitudinal portion (33) in order to achieve at least one given tension on the longitudinal portion (33).

In selected embodiments, the linking element (3) includes two hollow tubes (34) that each includes an internal conduit in which is mounted an elastic longitudinal portion (33) of the dampening element (31), said elastic longitudinal portion (33) having a length that is substantially greater than the length of the linking element (3), with the two ends of the longitudinal portion (33), protruding from the hollow tubes (34), each being held fixed in relation to the tubes (34) using fasteners (330, 331) of the longitudinal portion (33).

In selected embodiments, the rigid elements are solid bars, each having an end cooperating with the fasteners, such as clamps (20), of the implants (2) and an end cooperating with the central portion (32), the elastic longitudinal portion (33) being parallel to these hollow tubes and having a length substantially greater than the length of the linking element (3).

In selected embodiments, the solid bars comprise a groove, channel, or chute allowing the insertion of the longitudinal portion (33), the fasteners, such as clamps (20), thus resting on the solid bars (34) and not on the longitudinal portion (33).

In selected embodiments, the groove, channel, or chute extends, at the fixation extremity of the solid bars (34) cooperating with the clamps (20), by a hole allowing the insertion of the longitudinal portion (33), the groove being closed by a surface for supporting the fasteners, such as clamps (20).

In selected embodiments, the central portion (32) and the longitudinal portion (33) of the dampening element (31) form a unitary block, with the junctions between the central portion (32) and the longitudinal portion (33) of the dampening element (31) forming recesses, each accepting one end of one of the rigid elements (34).

In selected embodiments, the central portion (32) and the longitudinal portion (33) of the dampening element (31) comprise a unitary weave or braid of synthetic fibers, in which the size of the links of the weave or of the plaits of the braid is substantially identical on the two portions (32 and 33), which therefore have the same elastic properties.

In selected embodiments, the elastic properties of the central portion (32) and of the longitudinal portion (33) of the dampening element (31) are different, although they form a unitary block, due to a weave or braid having different degrees of tightness in the two portions (32 and 33).

In selected embodiments, the central portion (32) and the longitudinal portion (33) of the dampening element (31) are two separate elements, the central portion (32) being hollow and having an inside diameter that is substantially identical to the outside diameter of the longitudinal portion (33).

In selected embodiments, the central portion (32) and the longitudinal portion (33) of the dampening element (31) each comprise a weave or braid of synthetic fibers, with the size of the links of the weave or of the plaits of the braid being substantially identical on the two portions (32 and 33), which therefore have the same elastic properties.

In selected embodiments, the elastic properties of the central portion (32) and of the longitudinal portion (33) of the dampening element (31) are different, due to a weave or braid having different degrees of tightness in the two portions (32 and 33).

In selected embodiments, the two weaves or braids of the central (32) and longitudinal (33) portions are stitched together.

In selected embodiments, the central portion (32) and the longitudinal portion (33) comprise different materials.

In selected embodiments, the inside diameter of the central portion (32) is substantially smaller than the inside diameter of the hollow tubes (34) of the linking element (3), the outside diameter of the longitudinal portion (33), at the central portion (32), being substantially identical to the inside diameter of the central portion (32) and, at the hollow tubes (34), being substantially identical to the inside diameter of the hollow tubes (34).

In selected embodiments, the inside diameter of the central portion (32) and the outside diameter of the longitudinal portion (33) are substantially identical to the inside diameter of the hollow tubes (34) of the linking element (3).

In selected embodiments, the central portion (32) includes, close to its centre along the longitudinal axis (L), at least one slot (320) or cutout, located on at least one surface of the linking element (3) and facilitating the bending of the latter during movement of the patient on which the device (1) is intended to be implanted.

In selected embodiments, the central portion (32), on either side of its centre along the longitudinal axis (L), includes a chamfer (321) facing each of the rigid elements (34) located on at least one surface of the linking element (3) and facilitating the bending of the latter during movement of the patient on which the device (1) is intended to be implanted.

In selected embodiments, the two rigid elements (34), at their end in contact with the central portion, include (32) a rounded external profile (341) that fits onto a recess (322) of complementary shape inside the central portion (32), this complementarity of shape facilitating the movement of the rigid elements (34) in relation to the central portion (32), during the bending of the linking element (3) in the course of any movement of the patient on which the device (1) is intended to be implanted.

In selected embodiments, the hollow tubes (34) comprise, at their ends in contact with the central portion (32), on the one hand, a rounded external profile (341) that fits onto a recess (322) of complementary shape inside the central portion (32), this complementarity of shape facilitating the movement of the rigid elements (34) in relation to the central portion (32), during the bending of the linking element (3) in the course of any movement of the patient on which the device (1) is intended to be implanted and, on the other hand, and a flared internal profile (342), avoiding the compression and cutting of the longitudinal portion (33) inside the hollow tubes, during this bending.

In selected embodiments, the dampening element (31), on at least one part of at least one of its surfaces, includes at least one bending stop (310, 311) opposing the bending of the linking element (3) during movement of the patient on which the device (1) is intended to be implanted.

In selected embodiments, the bending stop (310, 311) is made from an elastic material to partially oppose the bending of the linking element (3).

In selected embodiments, the bending stop (310, 311) is made from a rigid, inelastic material to totally oppose the bending of the linking element (3).

In selected embodiments, the rigid elements (34) includes at least one flat (340), on at least one of their surfaces and at least at the position of the clamps (20), said flat (340) cooperating with the clamps (20) so as to prevent the rotation of the rigid elements (34) around their longitudinal axis (L).

In selected embodiments, the osseous anchoring implants (2) include anchors (21) that are used to attach the implants (2) to the vertebrae and each includes a conduit (22) intended to accept the linking element (3), with the fasteners such as clamps (20) including means for tightening the linking element (3) against an internal wall of the conduit (22), the cooperation between these means for tightening and the conduit (22) being used to hold the fixed angle between the longitudinal axis (L) of the linking element (3) and the dorsoventral axis of the vertebrae.

In selected embodiments, the fasteners (330, 331) of the longitudinal portion (33) include at least one removable lock, staple, ring, clip, pin, or stitch (330), clamping at least one end of the longitudinal portion (33).

In selected embodiments, the fasteners (330, 331) of the longitudinal portion (33) include at least one removable lock (300) that fits onto at least one hole passing through the longitudinal portion (33), along an axis that is substantially perpendicular to the longitudinal axis (L), where this hole constitutes a tension mark that is used to determine the tension of the longitudinal portion (33).

In selected embodiments, the fasteners (330, 331) of the longitudinal portion (33) include a fixing stop (331) with an outside diameter that is greater than that of the hollow tubes (34).

The present invention also provides various processes for the preparation of a vertebral support device having a dampening element, such as various embodiments of the present invention described herein. In such processes, the tension of one or more components of a dampening element is adjusted before the implantation of the device in accordance with the particular requirements of the implantation. The processes generally comprise the following steps:

placing a central portion of the dampening element between rigid elements of the dampening element;

placing a longitudinal portion of the dampening element along the rigid elements of the dampening element;

adjusting the tension of the longitudinal portion of the damping element; and fixing the longitudinal portion of the damping element in relation to the rigid elements of the dampening element.

In selected embodiments, the step of adjusting the tension of the longitudinal portion (33) is accompanied by a step of marking of at least one tension mark close to at least one of the ends of the longitudinal portion.

In selected embodiments, the step of fixing of the longitudinal portion (33) in relation to the rigid elements (34) by means of the fasteners (330, 331) includes a step of clamping of at least one end of the longitudinal portion (33) by a removable lock, staple, ring, clip, pin, or stitch (330).

In selected embodiments, the steps of adjusting the tension and for fixing of the longitudinal portion (33) includes a step of inserting at least one removable lock (300) in at least one hole drilled in the longitudinal portion (33), along an axis that is substantially perpendicular to the longitudinal axis (L), where this hole constitutes a tension mark that is used to determine the tension of the longitudinal portion (33).

In selected embodiments, the step of placement of the longitudinal portion along the rigid elements comprises a step of insertion of the longitudinal portion inside a groove, channel, or chute of the rigid elements.

In selected embodiments, the step of insertion of the longitudinal portion inside a groove, channel, or chute of the rigid elements is associated with a step of insertion of the longitudinal portion inside a hole extending the groove, channel, or chute at the fixation end of the rigid elements (34) at the level of the fasteners, such as clamps (20).

In selected embodiments, the step of placement of the longitudinal portion in relation to the rigid elements (34) comprises a step of insertion of the longitudinal portion inside a conduit of the rigid elements (34) which comprise hollow tubes and inside a conduit of the central portion, which is also hollow.

In selected embodiments, the step of fixing the longitudinal portion (33) includes a step of setting, on the end of the longitudinal portion (33) opposite to that including the removable locks, staples, rings, clips, pins, or stitches (330), a fixing stop (331) having an outside diameter that is greater than that of the hollow tubes (34).

In selected embodiments, the step of placement of the longitudinal portion in relation to the rigid elements comprises a step of insertion of the rigid elements, comprising solid bars, and of the central portion, inside the longitudinal portion (33) comprising an elastic sheath or sleeve.

In selected embodiments, the method comprises a step of adjustment of the position, along the longitudinal axis (L), of the rigid elements (34) with respect to the implants (2), followed by a step of blocking the rigid elements at the desired position by fasteners such as clamps (20).

In selected embodiments, the method comprises a step of adjustment of the orientation of the longitudinal axis (L) of the rigid elements with respect to the axis of the spinal column, followed by a step of blocking the rigid elements at the desired orientation by fasteners such as clamps (20).

BRIEF DESCRIPTION OF THE SEVERAL VIEWS OF THE DRAWINGS

The features and advantages of various embodiments and various aspects of the present invention will appear more clearly to those of skill in the art on reading the description that follows, with reference to the appended drawings in which.

DETAILED DESCRIPTION OF VARIOUS EMBODIMENTS

Figure 1:
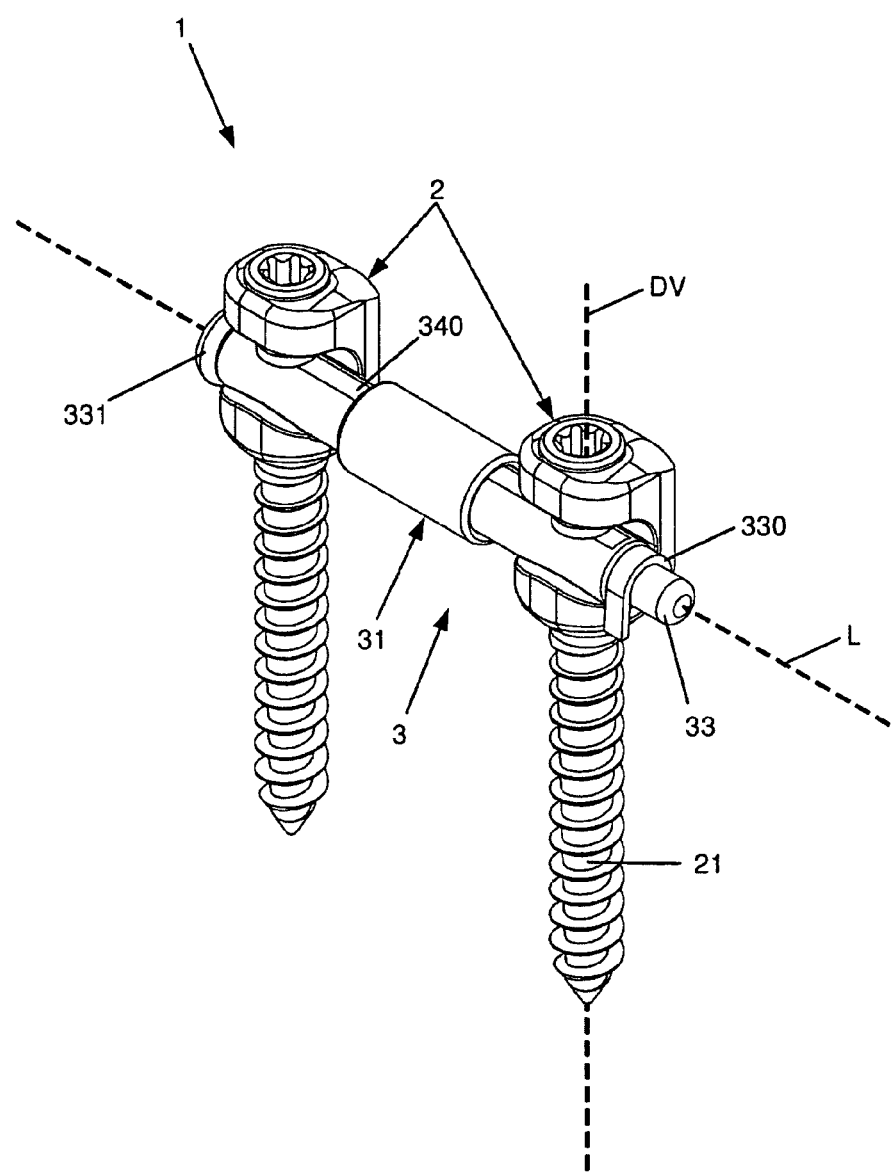
FIG. 1 shows a perspective view of one embodiment of a vertebral support device according to the invention.

This present invention concerns a vertebral support device such as, for example, the various embodiments of a device (1) as illustrated in FIGS. 1, 3A, 6A, 7A, 7B, 8A, 9, 10A, 10B, 11A, and 11B. The vertebral support devices of various embodiments of the invention are configured for implantation on at least two vertebrae, which may be adjacent or more remote, and are used to support these vertebrae in a given position, established during the implantation of the device, while still leaving these vertebrae with a certain freedom of movement about this position. A vertebral support device (1)

according to certain embodiments of the invention includes at least two osseous anchoring implants (2), each designed to be anchored to a vertebra. Often, each implant (2) is anchored to the pedicles of a vertebra along an axis called a dorso-ventral (DV) axis. A dorso-ventral (DV) axis is generally oriented along the dorso-ventral axis of the vertebra, which also can be called an antero-posterior or sagittal axis, depending on the nomenclature employed. Accordingly, the insertion axis along which an implant (2) is anchored to a vertebra will be referred to herein as a "dorso-ventral axis (DV)." However, embodiments having different implantation locations and anchorage angles are within the scope of the invention, and those of skill in the art will recognize that such nomenclature is adopted solely for convenience of description and does not limit the scope of invention to implants anchored at any particular place or in any particular orientation.

A vertebral support device (1) according to certain embodiments of the invention also includes at least one linking element (3) attached to implants (2). In many embodiments, linking element (3) comprises at least two rigid elements (34) articulated by at least one elastic dampening element (31). A wide variety of embodiments of linking elements is within the scope of the invention, including without limitation those described here. For example, the linking element (3) may comprise one or several dampening elements (31) and one or several rigid elements (34) attached to the implants (2). Various embodiments within the scope of the invention may have a dampening element (31) comprising, depending on the embodiments, at least one elastic central portion (32) absorbing the compression stresses applied on the device (1) and/or at least one elastic longitudinal portion (33) absorbing the extension or flexion stresses applied on the device (1). In various embodiments, rigid elements (34) of linking element (3) are fastened to implants (2) by fasteners (20). Many embodiments use clamps, such as clamps (20) illustrated in FIGS. 2, 6A, 9, 10B, and 11B, but other fasteners that generally can be used to fasten rods to vertebral anchoring implants may be substituted, as discussed further below. Various embodiments of the invention can include plural linking elements (3). For example, linking elements (3) can be generally parallel to each other to support two vertebrae on either side of the sagittal plane, or be aligned to support several successive adjacent vertebrae, as will be explained later.

Linking element (3) can have any elongated shape. Regardless of its shape, linking element (3) can be considered to comprise a dorsal face (or surface), a ventral face (or surface), and two lateral faces (or surfaces) with respect to a device (1) that is implanted along the dorsal faces of the vertebrae, even if the linking element does not necessarily comprises 4 faces (or surfaces). A device (1) within the scope of the present invention can also be implanted along the ventral faces of the vertebrae, but such installation generally is not preferred due to the presence of large blood vessels. Accordingly, the directional references used herein, including the foregoing as well as references to various planes such as the frontal plane and the sagittal plane, are specified with reference to a device (1) installed along the dorsal faces of the vertebrae. Those of skill in the art readily will appreciate the appropriate adjustments for directional references with respect to a device (1) implanted along the ventral faces of the vertebrae or elsewhere. Thus, a reference to a dorsal, a ventral, or a lateral face for surface of a component is solely a reference to an exterior part of the component having an orientation consistent with a frame of reference for a device (1) installed along the dorsal faces of the vertebrae.

The linking element (3) generally can be considered to have a "longitudinal axis (L)" since it links implants (2) and comprises at least one dampening element (31). This specification uses the nomenclature "longitudinal axis" as a general and nonlimiting reference to a direction in which an elongated object is elongated. For example, the linking element (3) generally can be considered to have a "longitudinal axis (L)" corresponding to its direction of its elongation it is in a "neutral" or "at rest" position, to the intended normal position of the vertebrae (i.e., no flexion, extension, lateral bending, rotation, or other displacement of the vertebrae) along which device (1) is (or will be) installed. In many implantations, longitudinal axis (L) will be oriented along the axis of the spinal column, but the linking element (3) may be disposed in other orientations. By way of nonlimiting example, the vertebrae generally follow a natural or pathological curve, and linking element (3) may be oriented in accordance with a natural curve or in accordance with correction of a pathological curve. In addition, the nomenclature "longitudinal axis" is not necessarily limited to a single, static linear direction. For example, as discussed below the linking element (3) can be installed having a neutral position in which the linking element (3) is bent in its neutral position, in may be considered to have a "longitudinal axis" corresponding generally to the bend or to have a localized "longitudinal axis" in various areas, such as, for example, one or both of the rigid elements (34) or the dampening element (31).

Figure 14A:
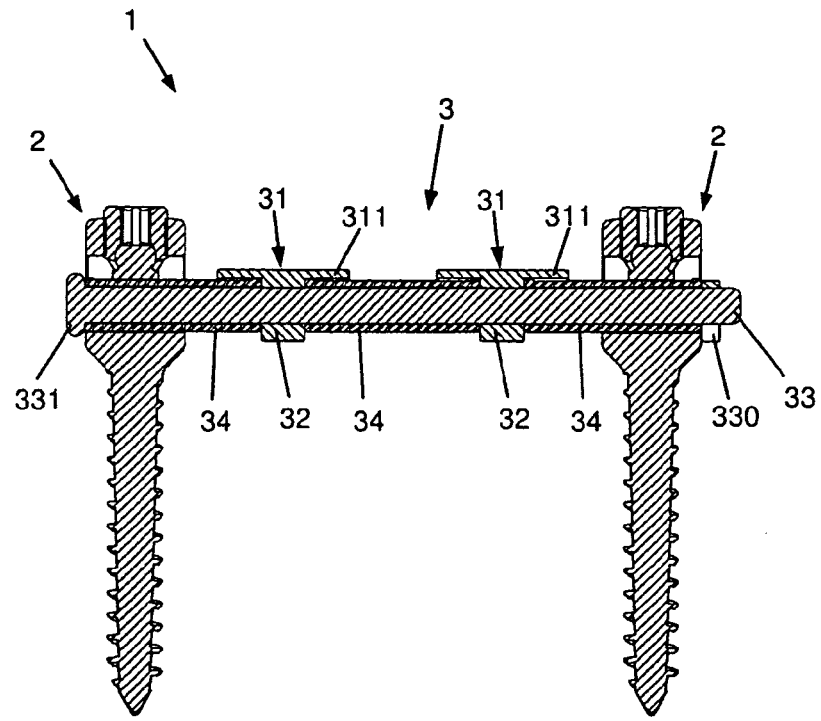
FIGS. 14A and 14B show, respectively, a longitudinal cross sectional view and a perspective view of two embodiments of a vertebral support device according to the invention in which the linking element comprises two dampening elements.
Figure 14B:
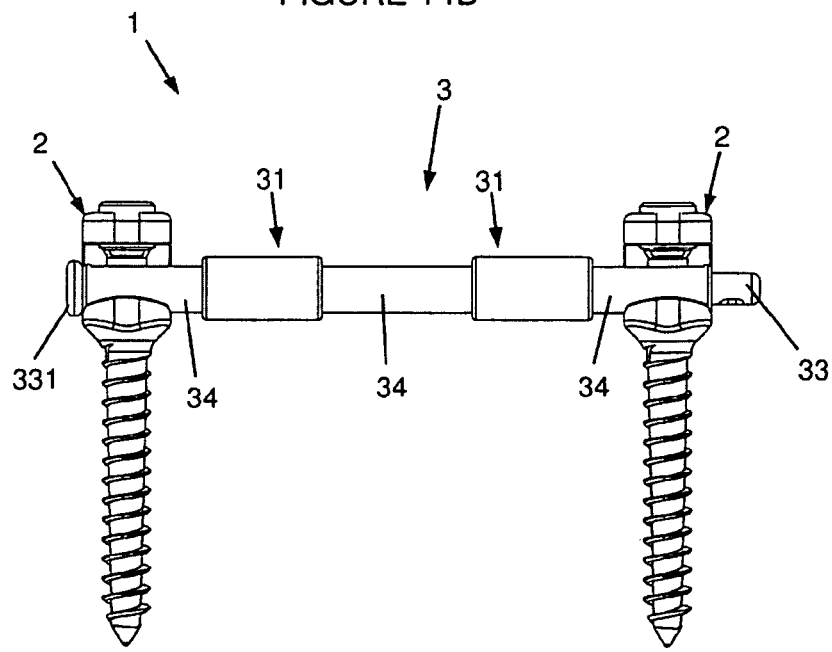
Figure 16:
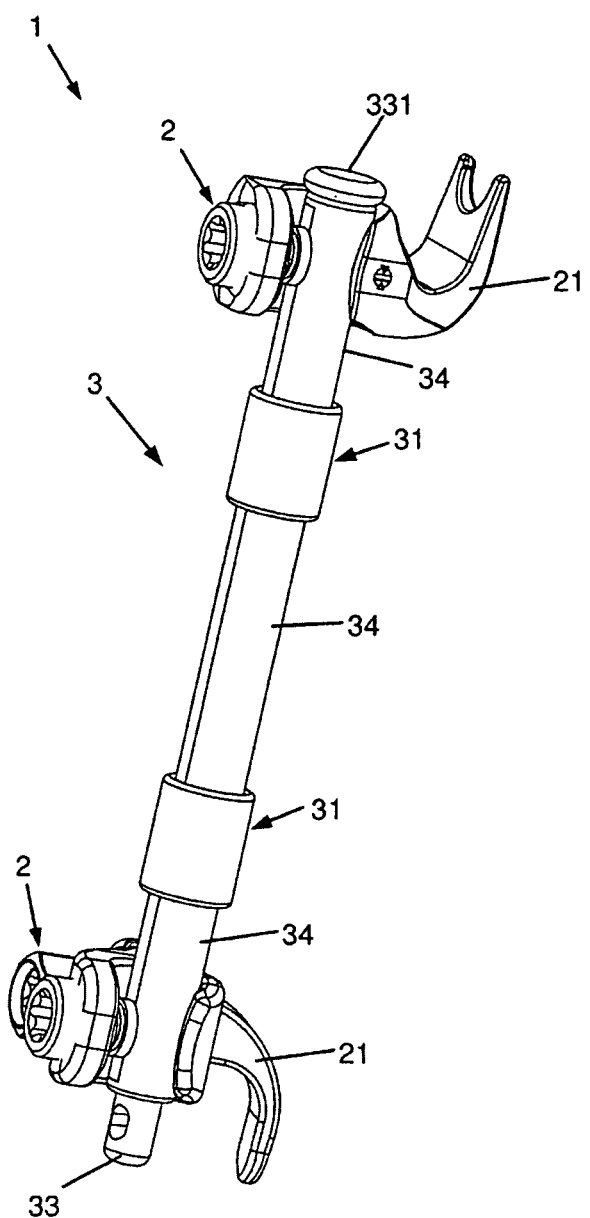
FIG. 16 shows a perspective view of an embodiment of a vertebral support device according to the invention in which each of the implants comprises a hook for attachment to the vertebrae.

Articulation of the rigid elements (34) by the dampening element (31) offers, in many embodiments, a certain degree of freedom of movement to the patient on which the device (1) is implanted, absorbing the stresses experienced by the linking element (3) during these movement and tending to return the device (1) to its neutral position. In various embodiments, dampening element (31) comprises at least one central elastic portion (32) located between the two rigid elements (34) and cooperating with them to absorb compressive and other stresses and strains imposed on the linking element (3). The articulation of the two rigid elements (34) occurs about central elastic portion (32), which is located between the rigid elements. Alternative embodiment of a linking element (3) could include several dampening elements (31) located at given distances from each of the osseous anchoring implants (2), so as to still further increase the freedom of movement, in particular regarding torsion of the spinal column. Various embodiments of linking elements (3) may have multiple dampening elements. FIGS. 14A, 14B, and 16 show two non-limitative examples of possible embodiments of a device (1) including such a linking element (3) comprising two dampening elements (31). Many other variants and optional embodiments of multiple dampening elements (31) are possible within the scope of the invention, such as, for nonlimiting example, embodiments having different types of dampening elements and embodiments having varying positions of the various dampening elements (31) along the longitudinal axis (L) of the linking element (3).

The dampening element (31) also comprises, in exemplary embodiments, a longitudinal elastic portion (33) comprising two ends configured to absorb the stresses occurring on the linking element (3). In various embodiments, the ends of the longitudinal elastic portion (33) are fixed with respect to the implants (2) and/or the rigid elements (34) by fasteners (330, 331). Elastic forces of the central (32) and longitudinal (33) portions oppose to each other, facilitating support of the vertebrae while allowing the vertebra some freedom of movement and tending to return the vertebrae to the rest position.

In various embodiments of the invention, dampening element (31) will be composed of a weave (or a braid) of synthetic fibers. These particularly advantageous embodiments can facilitate accommodation by the dampening element (31)

of the stresses and strains imposed by movement of the vertebrae on which device (1) is attached and adjustment of the tension of dampening element (31) at rest in the device (1) as explained below. The stitches of this weave or the plaits of this braid can be tightened to varying degrees to adjust the elastic properties of the dampening element (31) according to a desired elasticity. The dampening element (31) of these embodiments also can be stitched, which can facilitate assembly of its constituting parts and/or its fixation to the rest of the device. Alternatively, the dampening element (31) can be configured from solid elastic material having characteristics suitable for accommodation of the stresses and strains imposed by movement of the vertebrae on which device (1) is attached and adjustment of the tension of dampening element (31) at rest in the device (1). Such an elastic material also can eventually be stitched for assembly in the device and/or for adjustment of its tension. Of course, the central (32) and longitudinal (33) portions can be realized in the same weave, braid, or solid material, as described below, but can also be realized with any combination of the materials described here or any equivalent material that is flexible or elastic. In addition, in some embodiments described below, the dampening element (31) will not necessarily be in direct contact with the surrounding tissue and thus can be made from non-biocompatible material, but in preferred embodiments a biocompatible material will be used. FIGS. 19A, 19B, 19C and 19D depict non-limitative examples of such braids or weaves.

In some embodiments of the invention, the longitudinal portion (33) and the central portion (32) are formed as a unit. In some of these embodiments, the junctions between the central portion (32) and the longitudinal portion (33) of the dampening element (31) form receptacles, each receiving one end of one of the rigid elements (34), as shown for example in FIGS. 3B and 4A where the rigid elements (34) are hollow tubes. The central portion (32) and the longitudinal portion (33) of the dampening element (31) in some of these embodiments collectively can comprise a single weave or braid of synthetic fibers, in which the size of the links of the weave or of the plaits of the braid is substantially identical in the two portions (32 and 33), which therefore have the same elastic properties. In other embodiments, the elastic properties of the central portion (32) and of the longitudinal portion (33) of the dampening element (31) can be different, although they form a single weave or braid of synthetic fibers, by varying the tightness of the links of the weave or of the plaits of the braid the two portions (32 and 33), or their size. Alternatively, the unit can be formed from a single block of solid elastic material, or can be constructed by fixing together a central portion (32) and a longitudinal portion (33) each comprising solid elastic material. Alternatively, the unit can comprise one component made of a weave or braid of synthetic fibers and another component made of solid elastic material. In these alternatives, the components can have elastic properties that are similar or not, depending on whether the components are connected together in a single block, by stitching or any other means, or on whether the components are constructed with different elastic properties.

Figure 2:
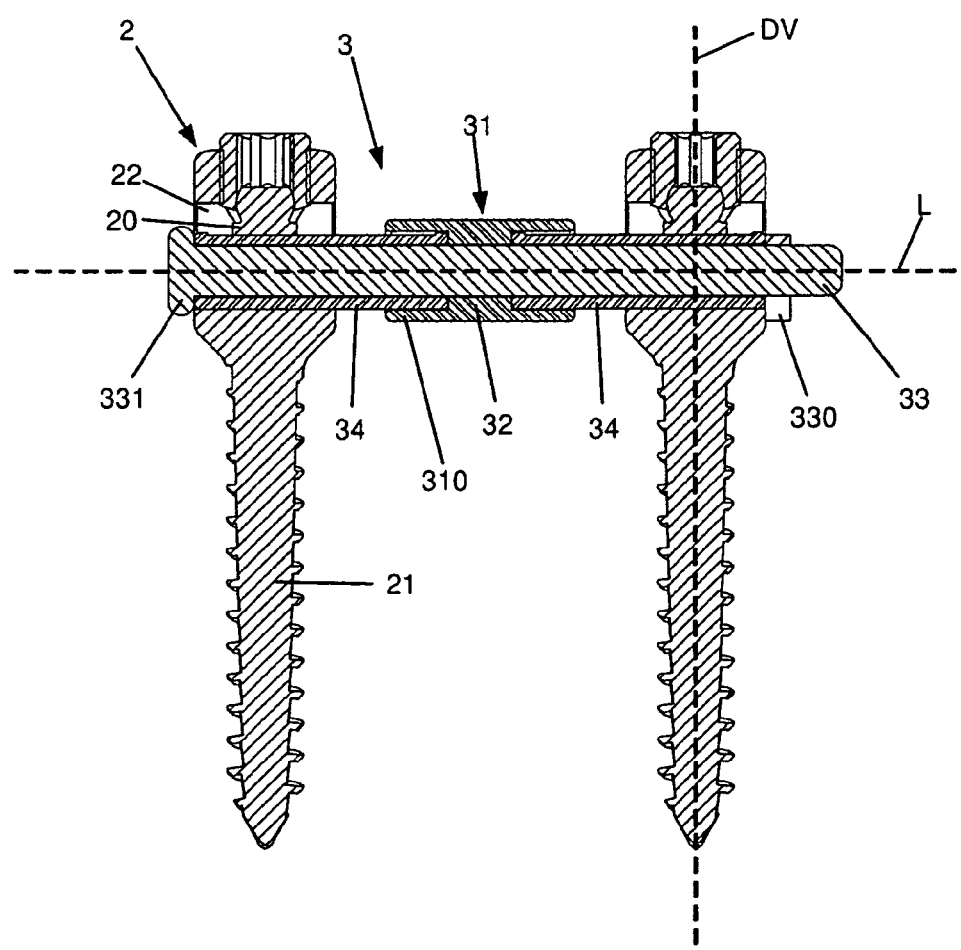
FIG. 2 shows a longitudinal cross sectional view of one embodiment of a vertebral support device according to the invention.
Figure 4A:
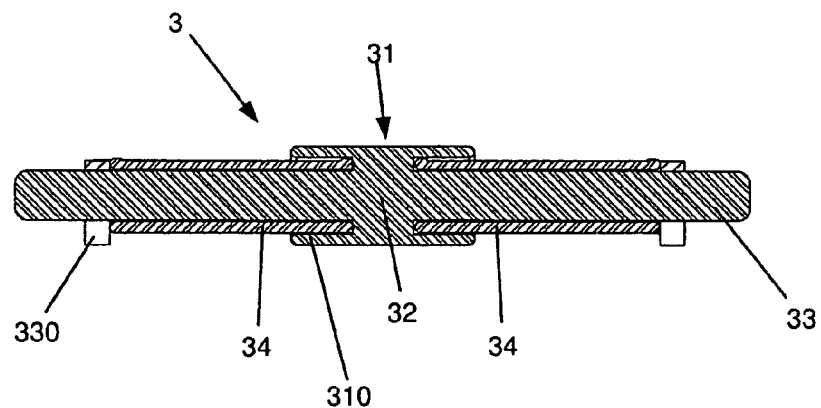
FIGS. 4A, 4B, and 4C show longitudinal cross sectional views of three different embodiments of the linking element of a vertebral support device according to the invention.
Figure 4B:
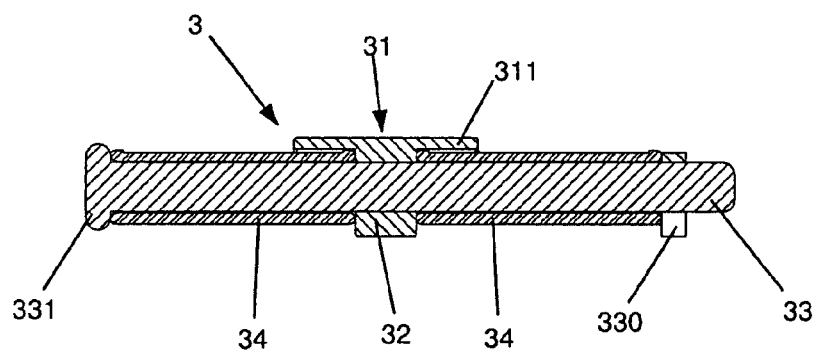
Figure 4C:
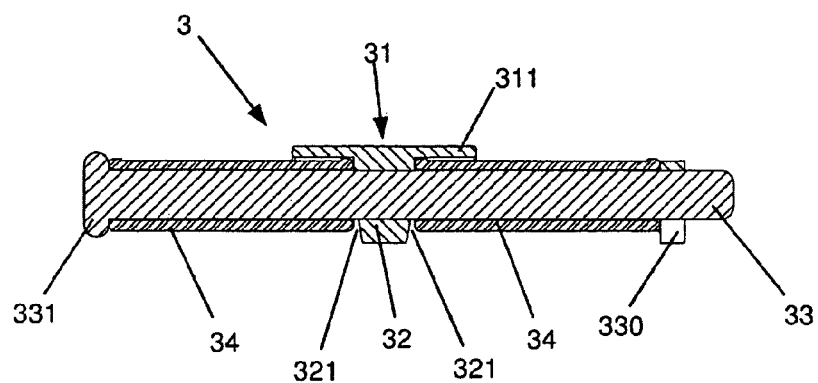
Figure 9:
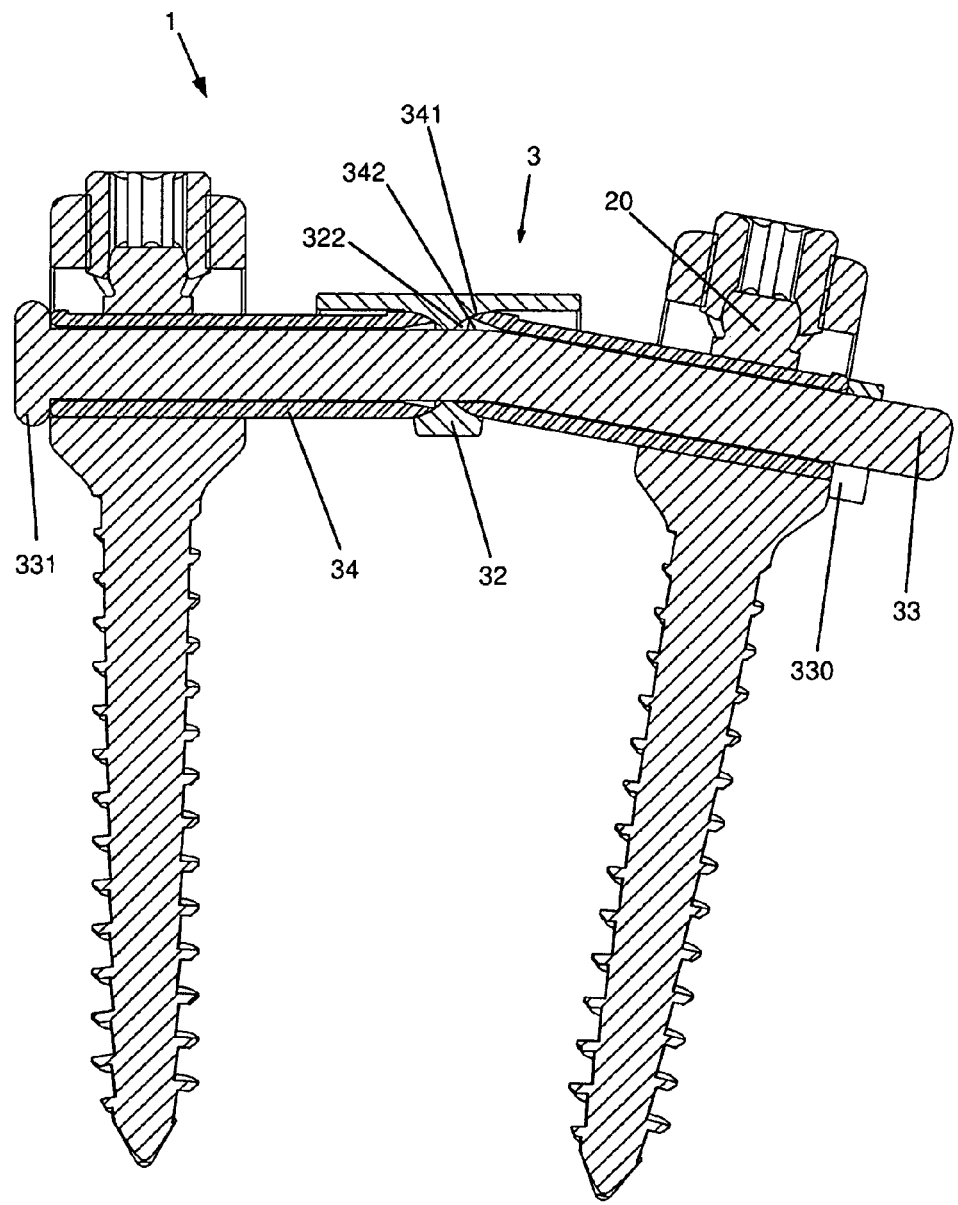
FIG. 9 shows a longitudinal cross sectional view of an embodiment of a vertebral support device according to the invention, with the device in a bent position.

In some embodiments, such as shown in FIGS. 2, 4B, 4C, and others, the central portion (32) and the longitudinal portion (33) of the dampening element (31) are two discrete elements. In some embodiments, the central portion (32) is hollow and has an inside diameter that is substantially identical to the outside diameter of the longitudinal portion (33). Thus, the central portion (32) mainly accommodates the compression stresses applied to the linking element (3), and the longitudinal portion (33) mainly accommodates the extension and torsion stresses applied to the linking element (3). Such stresses result, for example, from bending of the linking element (3) being damped by these two portions (32 and 33), as shown in FIG. 9. In a variant of this embodiment, the central portion (32) and the longitudinal portion (33) of the dampening element (31) will each be composed of a weave or braid of synthetic fibers, with the size of the links of the weave or of the plaits of the braid being substantially identical on the two portions (32 and 33) which therefore have the same elastic properties. In another variant, the elastic properties of the central portion (32) and of the longitudinal portion (33) of the dampening element (31) are different, due to a weave or braid that varies in the degree of tightness of the two portions (32 and 33). As previously, these two portions can be stitched together, regardless of the size of the links or of the braids of the synthetic fibers.

In the embodiments shown for example in FIGS. 4A and 4B, the inside diameter of the central portion (32) and the outside diameter of the longitudinal portion (33) are substantially identical to the inside diameter of the hollow tubes (34) of the linking element (3). Alternatively, the inside diameter of the central portion (32) can be smaller than the inside diameter of the hollow tubes (34) of the linking element (3), with the outside diameter of the longitudinal portion (33), at the central portion (32), being substantially identical to the inside diameter of the central portion (32) and, at the hollow tubes (34), being substantially identical to the inside diameter of the hollow tubes (34). During severe compression stresses, this alternative inhibits the inside edge of the ends of the hollow tubes (34) from sliding between the outer surface of the longitudinal portion (33) and the inner surface of the central portion (32).

Figure 6A:
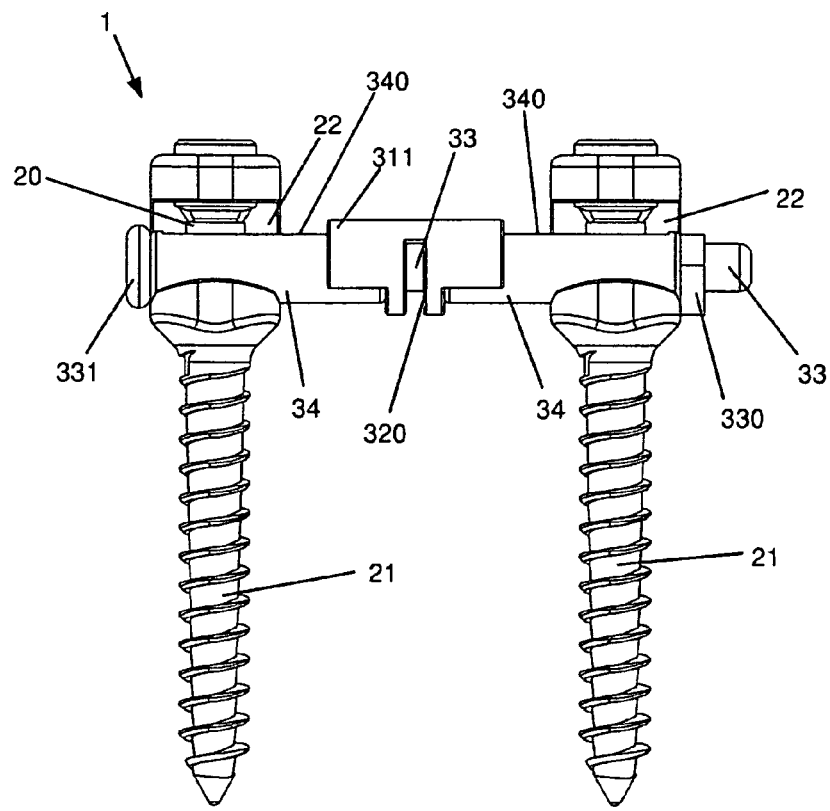
FIG. 6A shows an elevation view of one embodiment of a vertebral support device according to the invention.

Rigid elements (34) of the linking element (3) can comprise bars, tubes, rods, rails, or similar structures, whether straight or not, having cylindrical, polygonal, or other cross section, or indeed of any type of rigid structure adapted to the morphology of the spinal column of the patient on which the device is intended to be implanted. In some embodiments, a rigid element (34) includes at least one surface (340) configured to cooperate with a fastener fixing the rigid element (34) to an implant (2) to prevent rotation of the linking element (3) around its longitudinal axis (L). For example, FIG. 6A shows a flat surface, "flat (340)," on which a corresponding flat surface of clamp (20) bears. In various embodiments, flat (340) can be present on the entire dorsal surfaces of the rigid elements (34) or only on a part at which the rigid elements (34) are fastened to the implants (2) by means of the fasteners such as clamps (20). As shown in the figures, the fasteners (20) can be located on the implants (2) in order to fix the linking element (3) and allow an adjustment of the position, along the longitudinal axis (L), of the linking element (3) with respect to the implants (2). In addition, surface (340) can be configured in other geometries wherein cooperation of that surface with the fastener will prevent axial rotation of rigid element (34) about its longitudinal axis. The fixation of the linking element (3) to the implants (2) along rigid elements (34) reduces the risk of damage to linking element (3), compared to a direct fixation of the dampening element (31) to the implants (2).

In some embodiments of the invention, the rigid elements (34) of the linking element (3) can be tubes (34), each connected to an osseous anchoring implant (2) by the fasteners (20) and articulated by the dampening element (31) about a central portion (32) that fits onto each of the two tubes (34). The central portion (32) of the dampening element (31) can have an outside diameter that is about equal to the outside diameter of the tubes (34) of the linking element (3), but preferably the outside diameter will be greater to improve handling of the compressive stress imposed by the tubes (34), particularly when such stresses are not applied along an axis that is collinear with the longitudinal axis (L) of the linking element (3). Thus, in many advantageous embodiments, the central portion (32) of the dampening element (31) has an outside diameter that is, to varying degrees, larger than the outside diameter of the tubes (34) of the linking element (3).

In various embodiments of the invention, the rigid elements (34) of the linking element (3) are hollow and include an internal channel or conduit in which longitudinal portion (33) is mounted or otherwise disposed. In some embodiments, the channel or conduit and the longitudinal portion (33) preferably will be substantially cylindrical, but other geometries are possible, for example, a rectangular cross section that inhibits bending of the linking element (3) along its lateral surfaces. The longitudinal portion (33) may have an outside diameter or size that is substantially equal to the inside diameter or size of the channel or conduit in the rigid elements (34), or an outside diameter or size less than the inside diameter or size of the channel conduit to facilitate movement of the longitudinal portion (33) in the rigid elements (34) and handling of the stresses in extension (amongst others) applied to the linking element (3).

In some embodiments, the rigid elements (34) can comprise solid bars. For some of these embodiments, longitudinal portion (33) can be disposed along these bars, or inserted in a groove (or chute) longitudinally located on a surface of the bars, for example as described later in reference to FIGS. 10(A to C) and 11(A to C). In other embodiments, for example as illustrated in FIGS. 12A through 12D, bars (34) can be inserted inside an elastic longitudinal portion (33) that surrounds the rigid elements (34) and the central portion (32) much like a sheath. As with other embodiments, the central (32) and longitudinal portion (33) can be a single piece or plural separate pieces. The rigid elements (34) and the central portion (32) can be attached or not, with the longitudinal portion (33) being attached to the rigid elements (34), for example as detailed later in reference to FIGS. 12(A to D). If not attached together, central portion (32) and the rigid elements (34) nevertheless can be held together by the longitudinal portion (33) surrounding them, or central portion (32) and the rigid elements (34) can be attached by any mean, such as glue, threaded fastener, rivet, tongue and groove, or other connectors. In these embodiments, the longitudinal portion (33) can be maintained in tension and fixed to the rigid elements (34) by fasteners (330, 331), for example as described later. In other embodiments not shown, this longitudinal portion (33) of the linking element (3) can have a length that is substantially identical or slightly less than that of the assembly formed by the linking element (3) and can include, at its ends, fasteners inside the tubes, such as glue, threaded fastener, compression of its ends or any other fastener able to attach these ends solidly to the rigid elements (34).

Figure 6B:
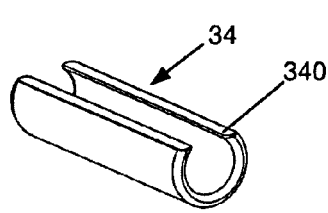
FIGS. 6B and 6C show two of the many different embodiments of rigid elements configured according to the invention.
Figure 6C:
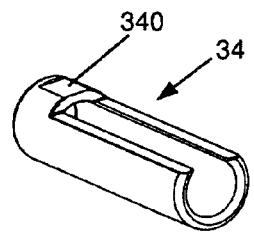

In some embodiments of the invention, as shown in FIGS. 6B and 6C, the rigid elements (34) are tubes open over at least one part of their length, for example to facilitate the insertion of the longitudinal portion (33) inside the tubes (34). The opening of the tubes (34) makes a transverse cross section generally having the shape of a "U" if the tubes are cylindrical or have a polygonal cross section. The opening of the "U" enables the insertion of the longitudinal portion (33) which can then be fixed, for example by fasteners (330, 331), with respect to the tube. In the embodiment shown in FIG. 6C, the hollow tube (34) is not open along its entire length and the closed portion can act cooperate with a fastener (330, 331). The closed portion also can comprise a flat (340) as shown or another type of surface cooperative with a fastener, for example clamp (20), fixing the rigid element (34) to an implant (2).

In the embodiment shown in FIG. 6B, the hollow tube (34) is opened along its entire length, and one of its extremities can cooperate with the fastener (330, 331) of the longitudinal portion (33). In the embodiment illustrated in FIG. 6B, the edges of the longitudinal opening form a substantially flat surface configured to cooperate with a fastener, for example clamp (20), fixing the rigid element (34) to an implant (2). In many of the embodiments, the longitudinal portion (33) of the linking element (3) has a length that is greater than the aggregate length of the two tubes (34) and the central portion (32), and the ends of the longitudinal portion (33), protruding from the rigid element (34) are fixed in relation to the tubes (34) by fasteners (330, 331). In certain embodiments, the tension of the elastic longitudinal portion (33) can be adjusted by adjustment of the relative position of the fasteners (330, 331) with respect to the elastic longitudinal portion (33). Thus, the position of at least one of the fasteners (330, 331) can be adjusted in the factory (with relatively precise measurement of the tension) or at the operating table by the surgeon, who can adjust the tension according to the configuration of the vertebrae on which the device is implanted.

Figure 3A:
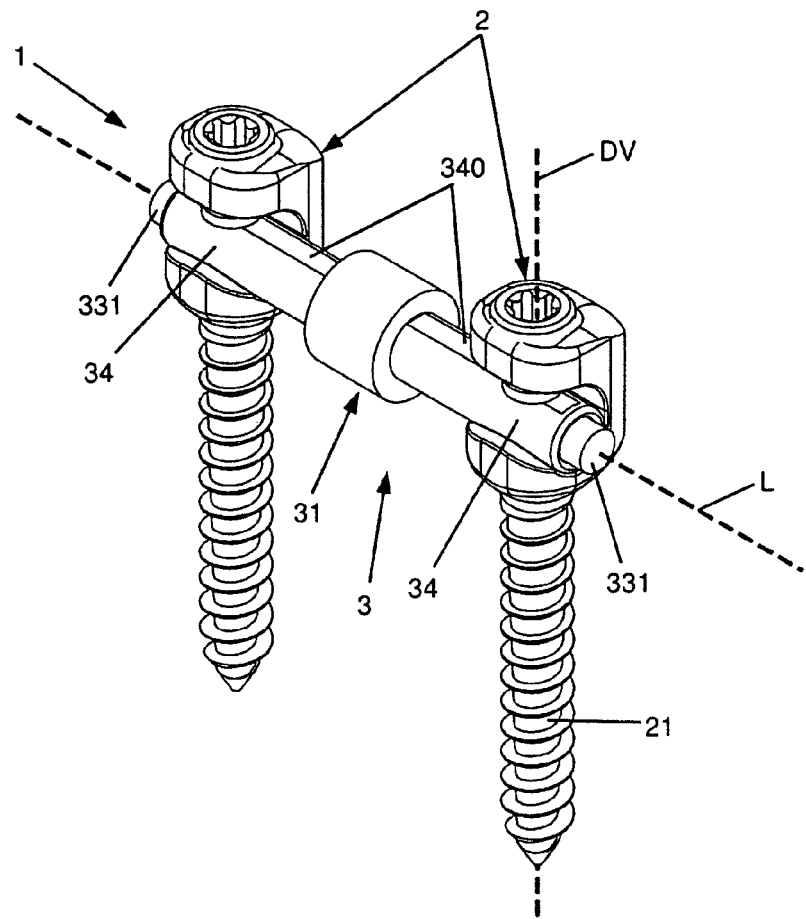
FIG. 3A shows a perspective view of one embodiment of a vertebral support device according to the invention.
Figure 8A:
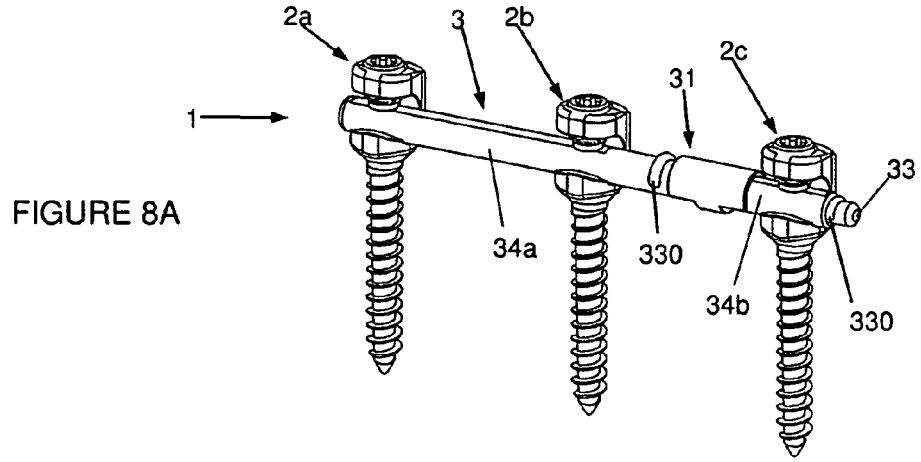
FIG. 8A shows a perspective view of one embodiment of a vertebral support device according to the invention.

In an embodiments such as shown in FIG. 1, for example, the fasteners (330, 331) can comprise at least one removable lock, staple, ring, clip, pin, or stitch (330), clamping at least one end of the longitudinal portion (33). In these embodiments, the ends of the longitudinal portion (33) can protrude from one or both ends of the hollow tubes (34), or can terminate within one or both of the tubes (34). FIG. 1, for example, shows a staple (330), but alternatives include structures such as a ring tightened around the end of the longitudinal portion (33) or any other removable lock, clip, pin, stitch or other fastener that can engage the end of the longitudinal portion (33) after its assembly with the rest of the device (1). For example, in some embodiments in which the rigid elements are hollow tubes (34), the fasteners (330, 331) for the longitudinal portion (33) can include at least one removable lock (330) that fits into at least one hole (330a) extending transversally through the longitudinal portion (33), along an axis that is substantially perpendicular to the longitudinal axis (L). The hole (330a) can be a tension mark used to determine the tension of the longitudinal portion (33), as shown for example on FIGS. 8A, 8D and 8E. The lock (330) can comprise lock, staple, ring, clip, pin, or stitch to be inserted into the hole, or other types of fasteners. A pin can be flared at its ends or fitted at its ends with stops to prevent it from leaving the hole, or its ends can include threads to mount a nut, or the pin can include any type of structure enabling it to be locked effectively in a given hole of the longitudinal portion (33) and thus maintain the latter in tension. Removable fasteners (330) also may comprise a stitching, such as a wire or filament passing through a hole (330a) extending transversally through the longitudinal portion (33) and passing through holes (or drilling) (330b) made in the rigid elements (34), as shown in FIGS. 8A, 8D and 8E. Those of skill in the art will recognize that the term "hole" or "drilling" can designate any type of channel passing through the longitudinal portion (33). The two ends of the longitudinal portion (33) can be equipped with this type of removable fastener, as shown in FIG. 4A, but a removable fastener (330) also can be used on one end only, in association with a non-removable lock (331) on the other end, such as a fixing stop for example. Thus, in some variant embodiments, the fasteners (330, 331) for the longitudinal portion (33) will include, at the end of the longitudinal portion (33) opposite to that which includes the removable fastener (330), a fixing stop (331) that comprises a widening of the longitudinal portion (33), where this fixing stop (331) has an outside diameter that is greater than that of the hollow tubes (34), as shown in FIGS. 1, 2 and 3A for example.

In the embodiments comprising a longitudinal portion (33) having a length greater than the aggregate length of the rigid elements (34) and the central portion (32), and extending beyond the extremities of the tubes, adjustment of the tension is facilitated by the fact that the tension varies as a function of the length of the longitudinal portion (33) extending beyond the extremities of the rigid elements (34) (whether hollow or solid). Nevertheless, the longitudinal portion can have a length adapted not to extend beyond the length of the rigid elements (34). In some embodiments, the rigid elements (34) can comprise holes (or bores or drillings) (330b), as shown in FIGS. 8D and 8E, with fasteners (330, 331) being configured for insertion in such holes to clamp the longitudinal portion (33) after adjustment of its length (and thus of its tension). For example, when the rigid elements (34) are hollow tubes in which the longitudinal portion (33) is inserted, or when the rigid elements (34) are solid bars along which a sheath-like longitudinal portion (33) is disposed, fasteners (330) typically will penetrate the longitudinal portion (33) and the rigid element (34) to fix the longitudinal portion (33) to the rigid element (34). Furthermore, to allow adjustment of the tension, the elastic longitudinal portion (33) can include, in some embodiments of the invention, at least one tension mark used to identify at least one position at which the fasteners (330, 331) of the longitudinal portion (33) must be placed along the longitudinal portion (33), by pulling (stretching) the longitudinal portion, in order to achieve at least one given tension. Such tension mark typically will be close to at least one of end of the longitudinal portion (33), and may comprise, for example, marks or notches visible at the surface of the longitudinal portion when the latter extended beyond the extremities of the rigid elements (whether hollow or solid). In the embodiments in which the rigid elements are hollow tubes, the tension marks may also comprise holes extending transversally through the longitudinal portion (33), regardless of whether the longitudinal portion (33) is configured to extend beyond the extremities of the tubes (34). These holes will then enable the insertion of the fasteners (330, 331) through the longitudinal portion (33) for its fixation and for adjustment of its tension.

Figure 3B:
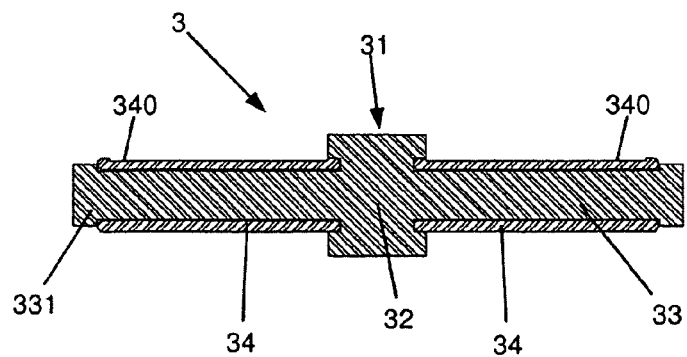
FIG. 3B shows a cross section view of the linking element shown in FIG. 3A.

In other embodiments, the ends of the longitudinal portion (33) each include a fixing stop (331) as shown in FIG. 3B. Factory configured devices (1) are particularly well suited to be equipped with fixing stops (331) at each end, and tension of the longitudinal portion (33) can be set during the assembly of the device (1) in the factory. In other embodiments, the ends of the longitudinal element (33) each comprise a fixing stop (331), and the rigid elements (34) are hollow tubes with a U-shape section as described previously for facilitating the assembly of the device. For such embodiments, the tension can be set at the factory by the location of the fixing stops (331), and the predetermined tension will be achieved upon assembly when the longitudinal portion (33) is inserted in the tubes (34), which can occur in the factory or in the surgical suite.

Implants (2) can take many forms such as, for example, the vertebral anchoring implants described in patent applications WO03/049629 and WO 2005/020829, submitted by the assignee of the present application, or other types of bone-anchoring implant such as, for example, those discussed in patent applications EP 0572790 or WO 00/15125 or U.S. Pat. No. 5,501,684, or other configurations that are suitable for anchoring to a vertebra and holding a bar (or any linking element) securely. Patent applications EP 0572790 and WO 00/15125 and U.S. Pat. No. 5,501,684 are incorporated herein by reference for all purposes. These different bone-anchoring implants (2) include anchors (21) such as a screw (21) intended to be screwed into a vertebra or a hook (21) intended to be inserted into suitable shapes on the vertebrae or recesses made especially in the vertebrae. FIG. 16 depicts a non-limitative example of a device (1) in which each of the implants (2) comprises a hook for anchoring, although alternative embodiments may have differing types of anchors, for example a device (1) comprising an implant having a screw and an implant having a hook. This type of hook is described in detail in reference to FIG. 7 of PCT Publication No. WO 03/049629 and to FIG. 4 of PCT Publication No. WO 2005/020829.

As noted above, the implantation axis of the implants (2) often is substantially parallel to the dorso-ventral axis of the vertebrae. Another implantation axis (DV), however, may be preferred in some installations (which, as discussed above, still may be referred to herein as a dorso-ventral (DV) axis), in which polyaxial osseous anchoring implants (2) such as, for example, those described in patent applications WO03/049629, WO 00/15125 and WO 2005/020829 may be used to advantage. Polyaxial osseous anchoring implants may allow use of the device (1) irrespective of the angle between anchoring axis (DV) of the implants (2) and longitudinal axis (L) of linking element (3). Polyaxial implants (2) also may be used to advantage for orientations of longitudinal axis (L) of linking element (3) other than along the axis of the spinal column. Thus, as mentioned previously, the fixation of the linking element (3) can be realized so that it follows the natural or pathological curve of the spinal column. In many of the embodiments of the invention, the angle between a longitudinal (L) axis of the linking element (3) in relation to the dorso-ventral (DV) axis of the implants (2) is fixed, after fixing the linking element (3) with the clamps (20) of the implants (2), regardless of the actual orientations of the longitudinal (L) and dorso-ventral (DV) axis (along the axis of the spinal column or not and, respectively, along the antero-posterior axis of the vertebrae or not). When such fixed angle is imposed, the dampening element (31) accommodates the stresses imposed on the assembly by movement of the vertebrae regardless of the orientations of the anchoring axes (DV) of the implants (2) or the longitudinal axis (L) of the linking element (3) and allows maintenance or restoration of the space between the vertebrae between which the device is implanted. Polyaxial implants may also be devised to permit some freedom of movement or the rod (or bar), even after the rod (or bar) is clamped to the implants. Such types of implants can be used within the scope of the instant invention, alone or in combination with other types of implants. For example, some embodiments may have each of the rigid elements (34) of the linking element (3) fixed to an implant (2) that allows some freedom of movement after the rigid element is clamped by the clamp (20). For another example, some embodiments may have one or more of the rigid elements (34) of the linking element (3) fixed to an implant (2) that allows some freedom of movement after the rigid element (34) is clamped by the clamp (20), with one or more of the other rigid elements (34) of the linking element (3) fixed to an implant (2) that imposes a fixed angle between a longitudinal (L) axis of the linking element (3) and the dorso-ventral (DV) axis of the implant (2) after the after the rigid element (34) is clamped by the clamp (20). In this example, the device (1) could still maintain or restore a space between the vertebrae on which it is implanted, but may allow more freedom of movement.

As shown in the figures, the osseous anchoring implants (2) include anchors (21) that are used to attach the implants (2) to the vertebrae. The implant (2) includes a conduit (22) configured to accept the linking element (3) and with fasteners, such as clamps (20), for fixing the linking element (3) against an internal wall of the conduit (22). The fasteners (20) generally can be a driven coupler, such as a screw, for example, or any type of known element that can secure linking element (3) to the implant (2). Each fastener (20) holds a rigid element (34) such that the longitudinal axis (L) of the linking element (3) extending through the rigid element (34) and the axis (DV) along which implant (2) is anchored to the vertebra establish a fixed angle. The fasteners, such as clamps (20) shown in the figures, can comprise a fixing screw that includes a flat at its base, intended to be in contact with the flat (340) on the linking element (3). As described in patent applications WO03/049629 and WO 2005/020829 incorporated herein, clamp (20) can comprise a ball and socket connection at its base, and/or the conduit (22) of the implant (2) receiving the linking element (3) can be flared and/or comprise a mobile baseplate. Structures such as these can provide a certain degree of freedom to the linking element (3) with respect to the implant (2) before their fixation. In many embodiments, the flat (340) is present on the dorsal surface of the linking element (3), since the clamps (20) are substantially collinear with the axis (DV) of the implants and rest against this dorsal surface of the linking element, but the flat (340) can be located differently according to the configuration of the clamps (20) or may not even be necessary. Clamps (20) can comprise a recess or a projection for engagement with a tool for tightening the clamps (20), such as, for example, a six-sided hole or stud, or a groove of a screw or a nut. Any type of fastener used to secure an implant to a link, either on the implant or on the link, can be used in alternative embodiments of the invention, to the extent that these fasteners allow a constant angle to be maintained between the longitudinal axis (L) of the linking element (3) passing through a rigid element (34) and the axis (DV) of the implant (2) to which the rigid element (34) is secured. The embodiments represented in the figures are particularly advantageous, since they use implants (2) of previous designs that facilitate the fitting of the device (1) by means of the degrees of freedom conferred by the clamps (20) before tightening and allow adjustment of the orientation of the rigid elements (34) as mentioned previously.

From the foregoing discussion, those of skill in the art will recognize that the dampening element (31) allows the device (1) to maintain the position of the implants (2) in relation to each other, while still providing some freedom of movement to the implants (2). Because of the dampening element (31), the support provided by the device (1) in various embodiments is relatively flexible and allows the vertebrae to be held in a desired position, thus offering relief to the intervertebral disc, while still leaving freedom of movement to the patient on which the device (1) is intended to be implanted.

The cooperation of the central portion (32) and of the rigid elements (34) also allows the distance between the vertebrae to be maintained, thus providing space between the vertebrae. This space, of course, can be substantially equal to the natural space between the vertebrae at rest, but if desired the space can be enlarged or reduced, even if the device is already implanted on the vertebrae, by enlightening the clamps (20), by separating or gathering the vertebrae with known tools, by adjusting the position of the rigid elements (34), and then by retightening the clamps (20).

In addition, fastening rigid elements (34) to implants (2) allows, in many embodiments, imposition of particular orientations on the linking element (3), unlike some other types of flexible support devices. Thus, for example, the linking element (3) can be installed having a neutral position in which the elastic dampening element (31) exerts a permanent force on the vertebrae when at rest, which in some embodiments is achieved by linking element (3) being bent in its neutral position. This aspect of various embodiments can facilitate accurate fitting of device (1) to the curve of the spinal column or correction of defects in the positions of the vertebrae.

Adjustable fixation of the rigid elements (34) to the implants (2) can provide additional advantages in various embodiments. For example, the length and position of the rigid elements (34) with respect to the implants (2) can be adjusted to vary the position of the articulation of the rigid elements (34) provided by the dampening element (31). Articulation can be centered, as illustrated respectively in FIGS. 21 and 20, with respect to the intervertebral space (IV) or with respect to the articular processes (AP) of the vertebrae, which is located lower than the center between the vertebral bodies. Other articulation positions may be preferred in some embodiments.

Figure 5A:
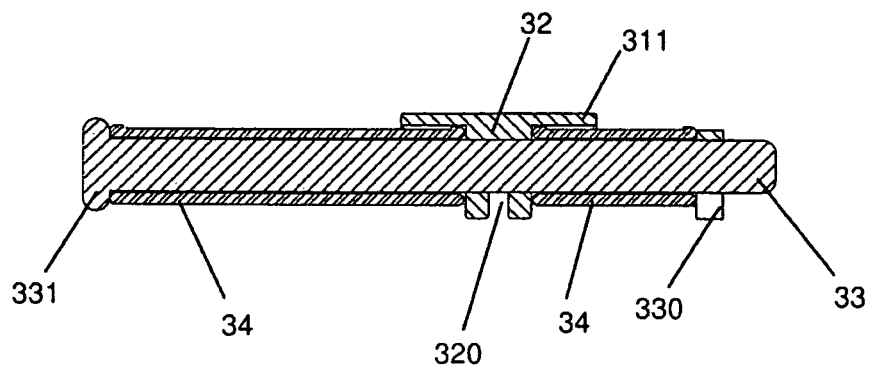
FIGS. 5A and 5B show longitudinal cross sectional views of two different embodiments of the linking element of a vertebral support device according to the invention.
Figure 20:
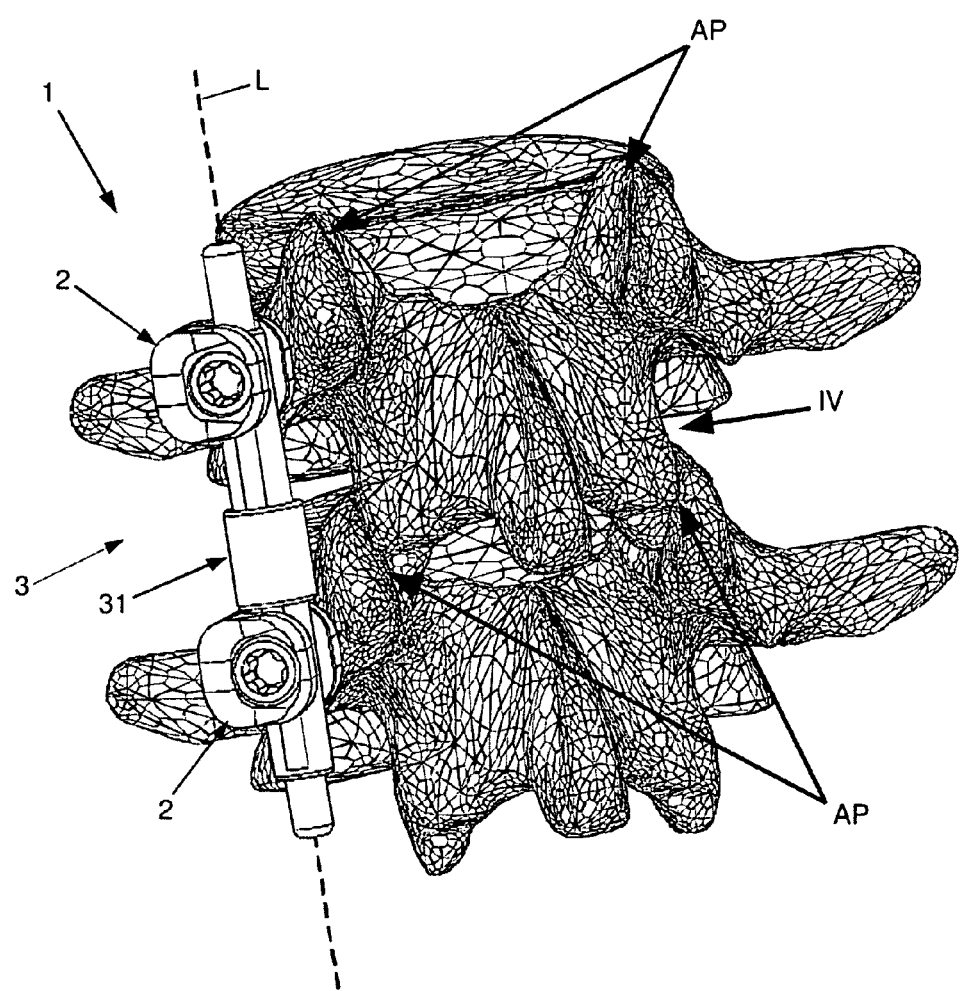
FIG. 20 show a perspective view of two adjacent vertebrae on which an embodiment of a vertebral support device according to the invention is mounted, wherein the dampening element is centered with the articular processes of the two vertebrae.
Figure 21:
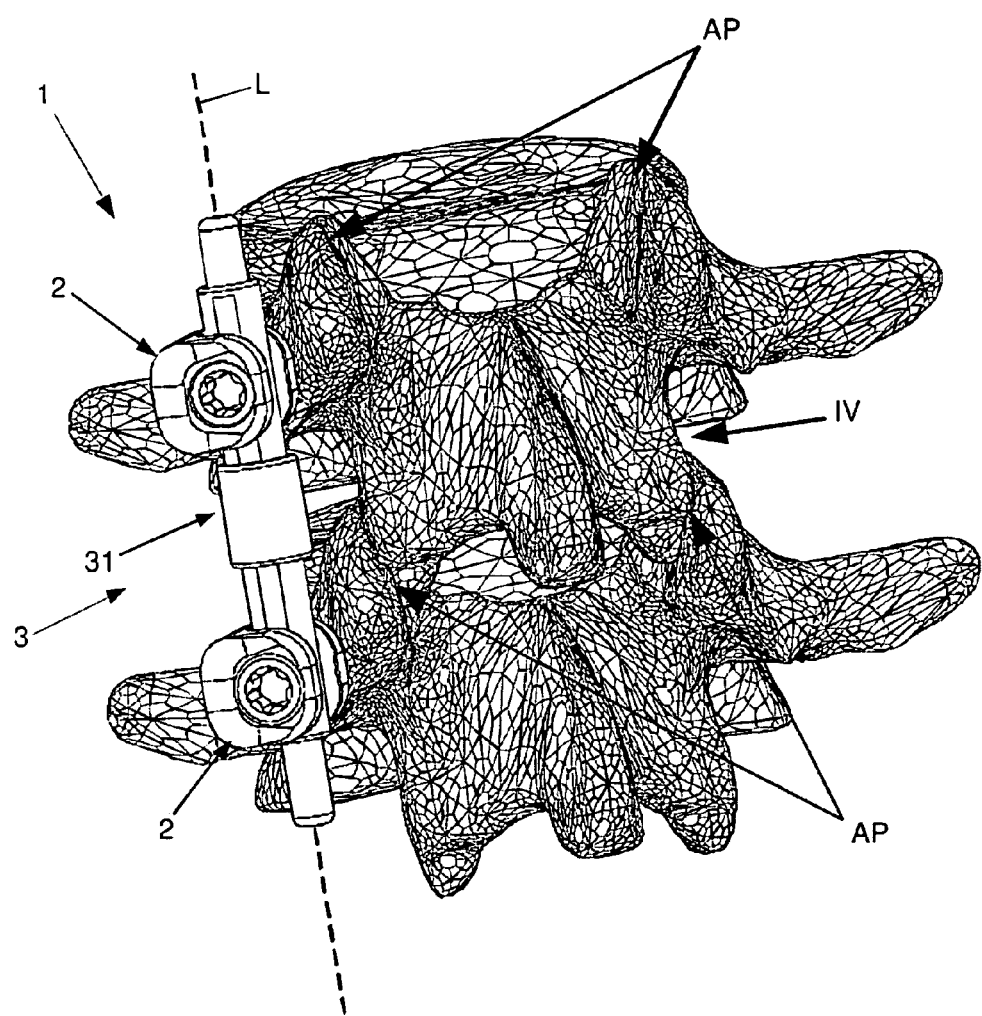
FIG. 21 show a perspective view of two adjacent vertebrae on which an embodiment of a vertebral support device according to the invention is mounted, wherein the dampening element is centered with the intervertebral space between the two vertebrae.

In various embodiment of the invention, the dampening element (31) is located on the longitudinal axis (L) of the linking element (3) substantially equally distant from each of the implants (2) between which it is located, thus centering the dampening element (31) between the implants (2). However, linking element (3) can have an off-center dampening element (31), as shown in FIG. 5A, which may be advantageous to adapt to the morphology of the patient on which the device (1) is implanted, and to optimize the stresses applied to the dampening element (31). Indeed, as mentioned previously, the articulation of the linking element (3) can be centered, for example, with respect to the articular processes (AP) rather than with respect to space (IV) between the vertebral bodies. In many embodiments, rigid elements (34) can have a variable length as illustrated in the non-limitative example of FIG. 5A and/or a variable position with respect to the implants, which allows adjustment of the position of the dampening element (31) with respect to the vertebrae. FIGS. 20 and 21 show two non-limitative examples of an embodiment of the device implanted on two adjacent vertebrae. In the example of FIG. 20, the dampening element (31) is centered relative to the articular processes (AP) between the vertebrae, whereas in FIG. 21, the dampening element (31) is centered relative to the intervertebral space (IV) between the vertebrae. Those of normal skill in the art will of course understand by reading the instant specification that the invention allows an adjustment of the different elements of the device (1) at any desired position and with any desired orientation and that the FIGS. 20 and 21 are given here only as illustrative examples.

Various embodiments can have rigid elements (34) configured with elongated regions suitable for engagement with fasteners (20) to fix the rigid elements (34) to the implants (2). By varying the point at which the rigid elements (34) are fixed to the implants (2), the position of the linking element (3) with respect to the vertebrae can be adjusted during the implantation of the device (1).

In the embodiment shown in FIG. 4C, for example, the central portion (32) includes, on either side of its centre along the longitudinal axis (L), a chamfer (321) facing each of the rigid elements (34) and located on at least one surface of the linking element (3). These two chamfers (321) facilitate the bending of the linking element (3) in the direction of the surface on which they are located during movement of the patient on which the device (1) is implanted. Facilitating such bending (or folding around the dampening element) of the linking element (3) may be desired to increase the degree of freedom of the device (1) in at least one direction. For example, in FIG. 4C, the chamfers (321) are present on the ventral surface of the central portion (32), which facilitates the bending of the linking element in the direction of this ventral surface and has the result of allowing the patient to lean forward more easily when the device (1) is implanted on the dorsal surface of the vertebrae. On the figures where these chamfers (321) are shown, they are located on only one surface, but the chamfers (321) could exist over the whole periphery of the central portion if an increase in the degree of freedom of movement of the device in all directions is desired. The angle of the chamfer can also be varied according to the degree of freedom wanted. Likewise, in other embodiments, the bending of the linking element can be facilitated by including at least one slot (320) or cut-out on the central portion (32), close to its centre along the longitudinal axis (L) located on at least one surface of the linking element (3), as shown for example in FIGS. 5A and 6A. This slot or cutout (320) can be disposed around all or part of the periphery of the central portion (32), and can extend through the whole thickness of the central portion (32), or through only a portion of the thickness of the central portion (32) if less facilitation of bending is desired.

Figure 5B:
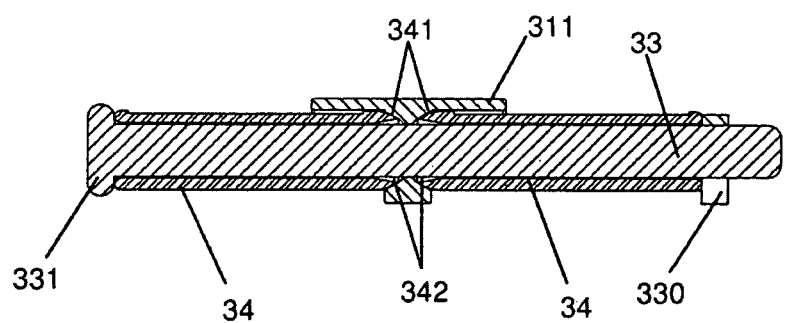
Figure 5C:
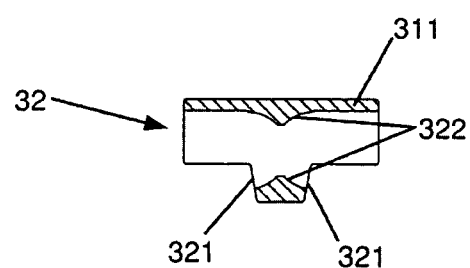
FIG. 5C shows a longitudinal cross sectional view of a central portion of the dampening element shown in FIG. 5B.
Figure 7A:
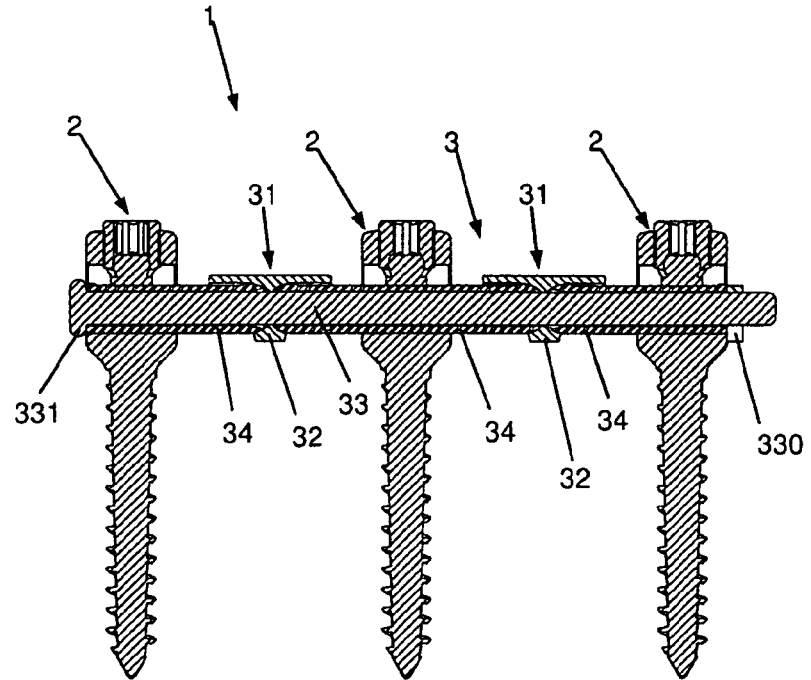
FIGS. 7A and 7B show longitudinal cross sectional views of two different embodiments of a vertebral support device according to the invention.

The bending of the linking element (3) in at least one direction can also be facilitated in some embodiments of the invention as shown in FIG. 5B, 7A or 9, for example, by including on the rigid elements (34), at their end in contact with the central portion (32), a rounded external channel (341) that fits into a recess (322) of complementary shape inside the central portion (32), as shown for example in FIG. 5C. This complementarity of shape facilitates the movements of the rigid elements (34) with respect to the central portion (32) during the bending of the linking element (3).

When the rigid elements (34) are hollow tubes, they may comprise a flared internal bore or channel (342) at the ends in contact with the central portion (32), as shown in FIG. 5B for example. FIG. 9 shows the device (1) during the bending of the linking element (3) in the course of any movement of the patient and clearly shows the advantage obtained with the flared internal bore or channel (342) of the hollow tubes (34), as well as by the fit between the rounded external channel (341) and the recess (322) of complementary shape inside the central portion (32). These two channels (341, 342) and this complementarity of shape facilitate the movement of the hollow tubes (34) in relation to the central portion (32).

Conversely, it is sometimes desirable to limit the bending of the linking element (3) in at least one direction. The dampening element (31) can then, in different embodiments, include at least one bending stop (310, 311) on at least one part of at least one of its surfaces. The bending stop (310, 311) will then oppose the bending of the linking element (3) in the direction of the surface on which this stop is located. In addition, it is possible to include a first type (310) of bending stop located on all the surfaces of the linking element (3) (i.e., all around the linking element (3)), which limits bending in all directions, or another type (311) of bending stop located only on one surface of the linking element (3), which limits bending along that surface. These bending stops (310, 311) can comprise an extension of the central portion (32) projecting from the rigid elements (34) or in separate elements, fixed onto the central portion (32). In some embodiments, the bending stops (310, 311) can comprise an elastic material that just partially opposes the bending of the linking element (3) or can comprise a rigid, inelastic material that totally opposes the bending of the linking element (3).

Figure 17:
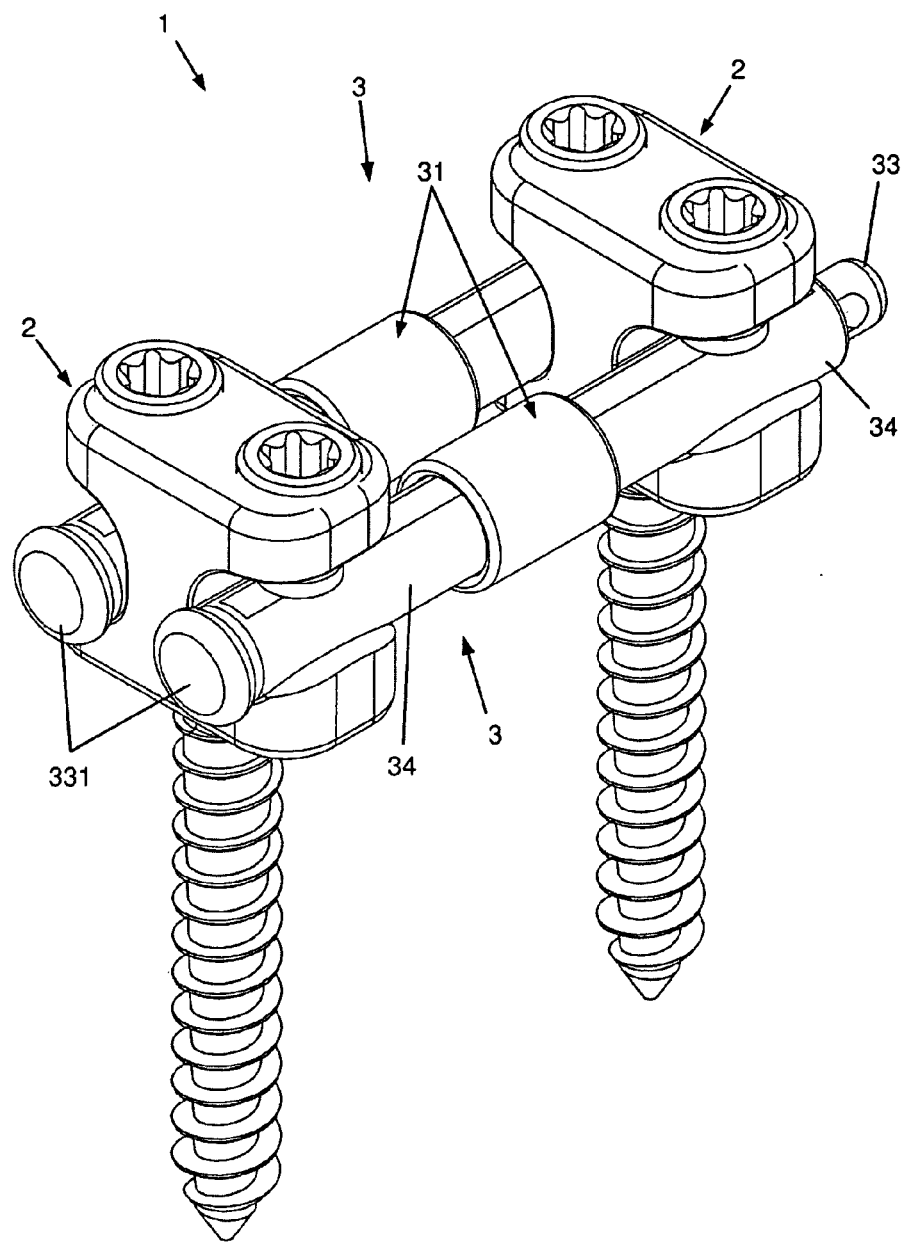
FIG. 17 shows a perspective view of an embodiment of a vertebral support device according to the invention having double-fixing implants fixing two linking elements substantially parallel to each other.
Figure 18A:
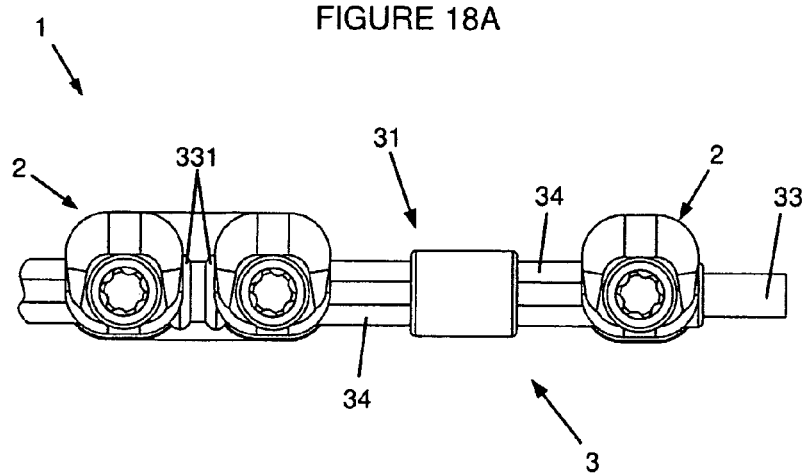
FIGS. 18A and 18B show, respectively, a upper view and a longitudinal cross sectional view of an embodiment of a vertebral support device according to the invention having double-fixing implants fixing two linking elements substantially collinear to each other.
Figure 18B:
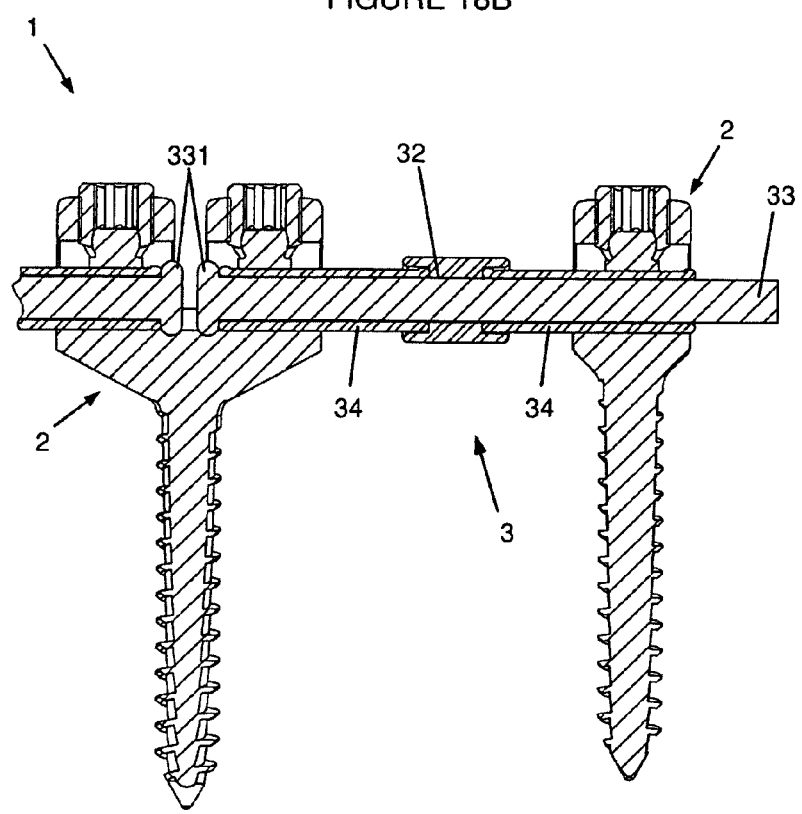
Figure 19A:
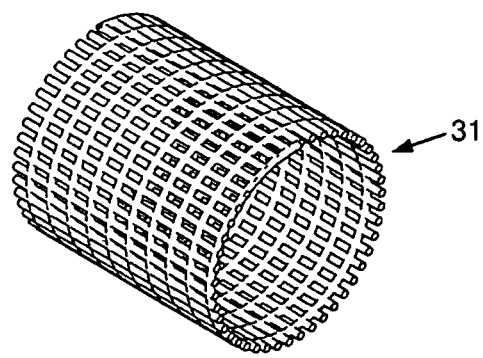
FIGS. 19A, 19B, 19C and 19D show, respectively, a perspective view, a side view and two detail views of 4 embodiments of weave or braids of a dampening element of a vertebral support device according to the invention.
Figure 19B:
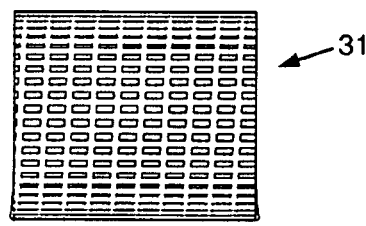
Figure 19C:
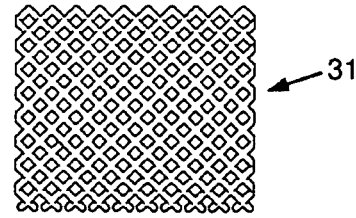
Figure 19D:
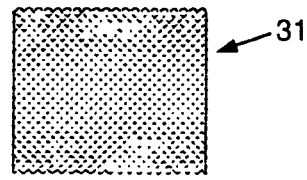

FIG. 7A depicts an embodiment of a device (1) to support three vertebrae. The device (1) in these types of embodiments includes three implants (2), each designed to be anchored to one of the vertebrae and connected together by a linking element (3) that has three rigid elements (34) (hollow tubes shown in this embodiment as a non-limitative example) and two dampening elements (31) between the three rigid elements (34). In this embodiment, the central rigid element (34) located between the two dampening elements (31) differs from the other rigid elements. For example, the central rigid element (34) in this embodiment is longer and includes two ends designed to fit the dampening elements (31). Another type of embodiment that can be used to support three successive adjacent vertebrae comprises a central implant (2) configured to fix two discrete linking elements (3). This embodiment would include this double-fixing implant, two normal implants (2) and two linking elements (3) that each includes a dampening element (31). Collinear linking elements (3) could be fixed end-to-end in the double-fixing implant, and non-collinear linking elements (3) could be fixed side-by-side in the double-fixing implant. FIG. 17 shows a non-limitative example of an embodiment of a double-fixing implant (2). In this example, the head of the implants comprises two recesses (or channels or conduits) intended to the respective rigid elements (34) of linking elements (3) substantially parallel to each other. Optionally, these linking elements may have different orientations by providing polyaxial fixing means, such as, for example, a ball and socket connection or a mobile base. FIGS. 18A and 18B show another non-limitative example of a possible embodiment of a double-fixing implant (2), in which the head of the implant is adapted to receive two collinear linking elements (3). Of course, the two linking elements (3) can also have an orientation different one of another since the head may comprise polyaxial means for independently fixing each of the two collinear linking elements (3).

Figure 7B:
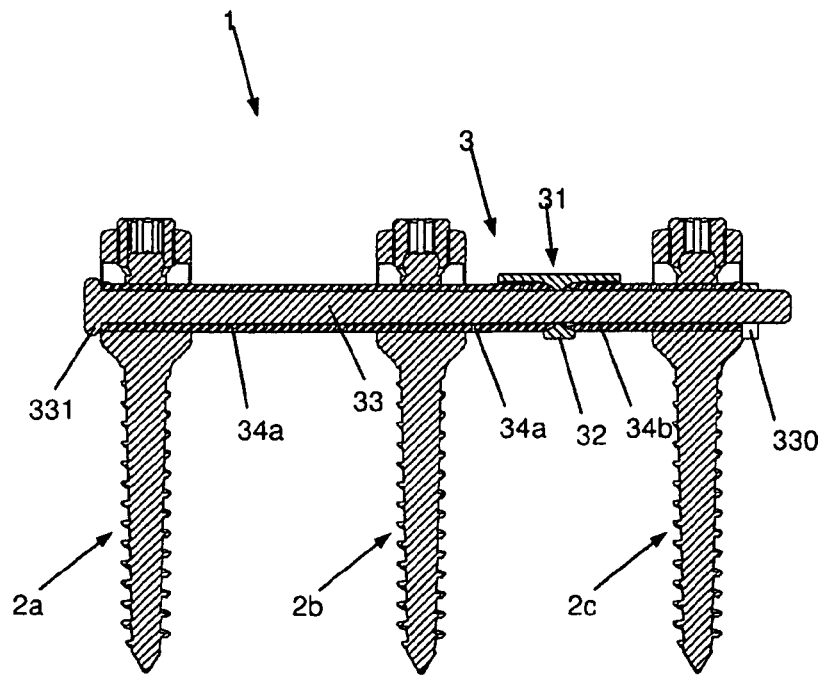

FIG. 7B depicts another embodiment of a device (1) to support three vertebrae. In this embodiment, however, the device (1) allows the arthrodesis (total immobilization and intervertebral fusion) of a first space between a particular vertebrae, and flexible support for another space between other vertebrae. In the illustrated embodiment, the linking element (3) includes a first rigid element (34a) (comprising, as a nonlimiting example, a hollow tube) connecting implants (2a) and (2b). The linking element (3) does not include a dampening element between implants (2a) and (2b), to firmly fix the respective vertebrae and allow arthrodesis. A dampening element (31) is disposed between implants (2b) and (2c), however, and connected to a second rigid element (34b) (also comprising, as a nonlimiting example, a hollow tube) fixed onto the third implant (2c). This configuration, which allows intervertebral fusion between the some vertebrae and provides support for another intervertebral space, will be particularly useful when the disc of the first intervertebral space is too damaged to be preserved, and therefore requires an intervertebral fusion, while the disc of the second space is damaged but can be preserved. In this embodiment, the second disc is flexibly supported, potentially preventing or slowing its total collapse.

In the embodiments illustrated in FIGS. 7A and 7B, longitudinal elastic portion (33) extends throughout linking element (3). FIGS. 8A to 8E also show embodiments of a vertebral support device for implantation on three vertebrae to allow the arthrodesis (complete intervertebral immobilization and fusion) of a first intervertebral space while flexibly supporting vertebrae on both sides of another intervertebral space, but in these embodiments the longitudinal portion (33) extents through only a portion of rigid element (34). The other portions of the rigid element (34) may then be solid, as shown in FIGS. 8C and 8E, but may well also be hollow, as long as the rigid element (34) comprises at least one opening on at least one of its surfaces for fixing the longitudinal portion (33) with respect to the rigid element (34). The opening can receive a fastener (330, 331), as detailed hereafter. For the vertebral space to be fused, linking element (3) need not comprise any dampening element (31), and the longitudinal portion (33) can adequately extend only between the implants (2) anchored to the vertebrae to be flexibly supported by the device (1) while still having a certain degree of freedom. Thus, in these embodiments, the linking element (3) comprises a first rigid element (34*a*) which can be solid or hollow, between a first and a second implant, and a second rigid element (34*b*) configured to accommodate longitudinal elastic element (33) (hollow, as a non-limiting example, in the illustrated embodiments). A dampening element (31) is disposed between first rigid element (34*a*) and second rigid element (34*b*). The extremity of first rigid element (34*a*) proximal to the dampening element (31) can, as shown in FIGS. 8C and 8E, be hollow and equipped with fasteners (330, 331) for the fixation of the longitudinal portion (33) inserted in this hollow extremity of the rigid element (34*a*).

Figure 8B:
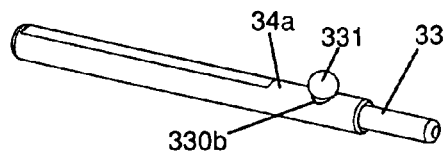
FIGS. 8B and 8C show, respectively, a perspective view and a longitudinal cross sectional view of one embodiment of a linking element of a vertebral support device.
Figure 8C:
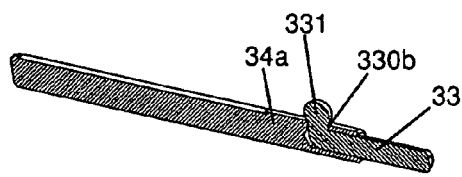
Figure 8D:
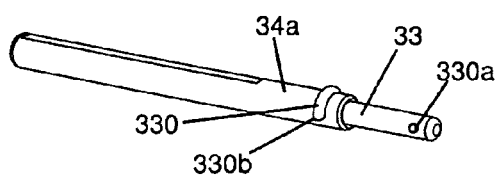
FIGS. 8D and 8E show, respectively, a perspective view and a longitudinal cross sectional view of the linking element shown in FIG. 8A.
Figure 8E:
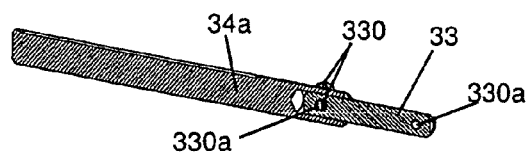

In the embodiment shown in FIGS. 8B and 8C, a fixing stop (331) provides the fixation of the longitudinal portion (33) with respect to this hollow extremity of the rigid element (34*a*). This stop (331) has a diameter larger than the diameter of the inner channel of the hollow portion of the first rigid element (34*a*) and larger than the diameter of an opening (330*b*) present on at least one of the surfaces (or one wall) of the rigid element (34*a*). In the embodiment shown in FIGS. 8D and 8E, removable lock (330) provides the fixation of the longitudinal portion (33) in the hollow portion of the first rigid element (34*a*). In the illustrated embodiment, removable lock (33) comprises a stitching (a wire or filament, for example) passing through a hole (330*b*) (or bore or drilling) extend through the walls of the rigid element (34) and at least one hole (330*a*) in the longitudinal portion (33). Thus, the removable lock comprises, in this example, a wire or filament (330) passing through the rigid element (34*a*) and the longitudinal portion (33). The longitudinal portion (33) can comprise a plurality of holes (330*a*) providing adjustment of its tension, as mentioned previously. Likewise, the other extremity of the longitudinal portion (33) can comprise the same type of fastener as used in other embodiments described herein, such as, for example, a wire (330) passing through the hole(s) (330*a*) extending through the longitudinal portion (33), as shown in FIG. 8A and suggested by FIGS. 8D and 8E. In another embodiment already mentioned, the extremity of the longitudinal portion (33), when it does not extend beyond the extremity of the rigid elements, can be fixed with removable lock (330) passing through the hole(s) (330*a*) extending through the longitudinal portion (33) and passing through the hole (or drilling) (330*b*) extending through the rigid element (34).

Figure 10A:
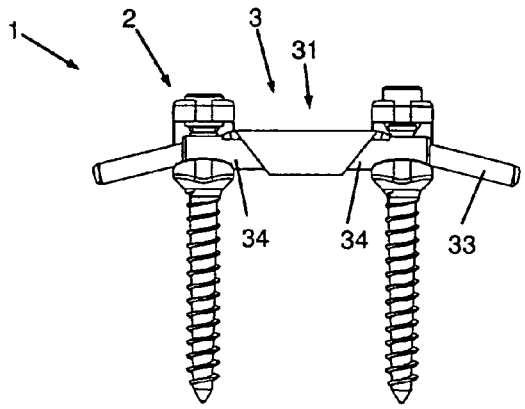
FIGS. 10A and 10B show, respectively, an elevation view and a longitudinal cross sectional view of another embodiment of a vertebral support device according to the invention.
Figure 10B:
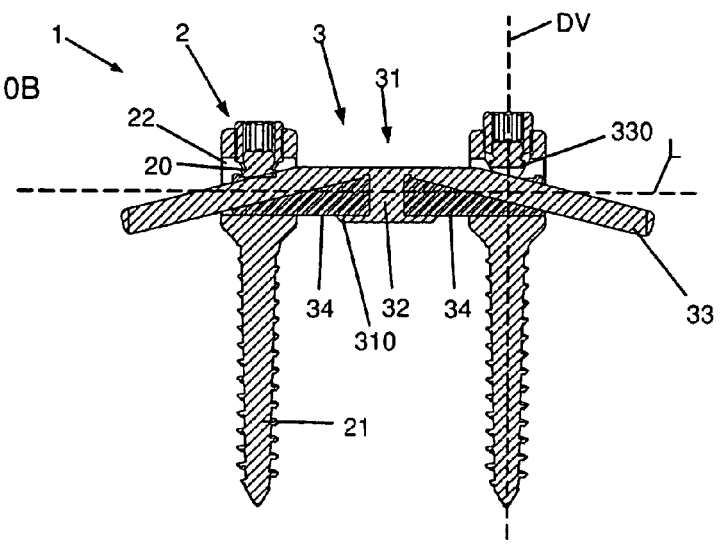
Figure 10C:
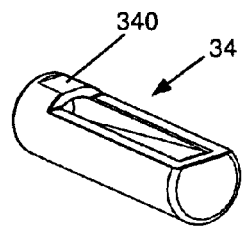
FIG. 10C shows a perspective view of one of the various types of rigid elements that can be used in this embodiment.
Figure 11A:
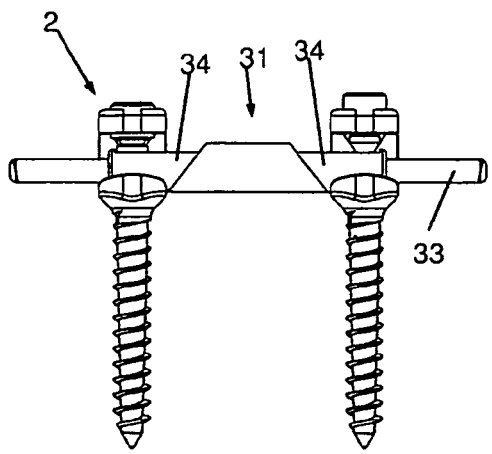
FIGS. 11A and 11B show, respectively, an elevation view and a longitudinal cross sectional view of another embodiment of a vertebral support device according to the invention.
Figure 11B:
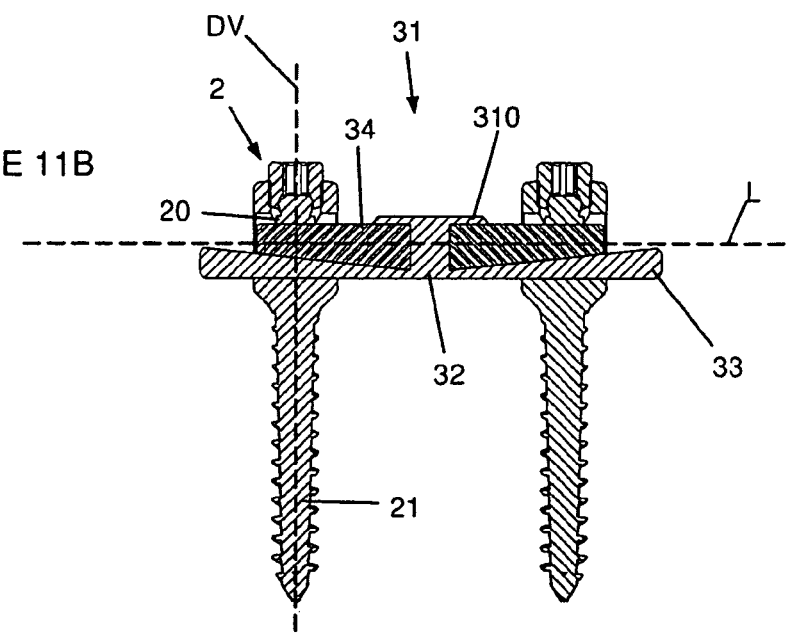
Figure 11C:
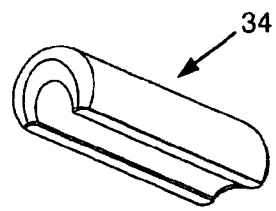
FIG. 11C shows a perspective view of one of the various types of rigid elements that can be used in this embodiment.

FIGS. 10A, 10B and 10C, as well as FIGS. 11A, 11B and 11C show various embodiments in which the rigid elements are solid bars, or at least partially solid, along some or all of their length. In these embodiments, each of the solid bars (34) comprises along one of its surfaces a groove, channel, or chute having a depth increasing from its central end, which cooperates with the central portion (32). In the embodiment of FIGS. 10(A to C), as particularly visible on FIG. 10C, at the regions which attach to the implants (2), the rigid element (34) actually comprises a hollow tube. At this point, the groove, channel, or chute is transversely enclosed by a surface that provides a support for the fixation of the rigid element. As in the previously presented embodiments, this support surface can comprise a flat (340) intended to cooperate with the clamps (20) of the linking element (3) and the implants (2). Thus, this surface forms a structure supporting the clamps (20), and the groove, channel, or chute proceeds through a hole allowing the insertion of the longitudinal portion (33).

In the embodiment of FIGS. 11(A to C), as particularly visible in FIG. 11C, the groove, channel, or chute is not enclosed and the rigid element (34) has a U-shape section along its entire length, the depth of the chute varying between the two extremities of the rigid element (34). In this embodiment, as visible on FIG. 11B, the groove, channel, or chute has at its ends a depth such that the longitudinal portion (33) can be inserted inside it without protruding from it. Thus, the lateral walls of the groove, channel, or chute form a surface supporting the fixation of the rigid element (34) without crushing elastic longitudinal portion (33).

In the embodiments illustrated in FIGS. 10(A to C) and 11(A to C), the longitudinal portion (33) is positioned along the rigid element (34) for part of its length and inside the rigid element (34) for another part of its length, thus leaving a surface for supporting the clamps (20) which do not crush the longitudinal portion (33). As described previously, the longitudinal portion can be maintained in tension and fixed by the fasteners (330, 331) adapted to its structure, for example where the longitudinal portion extends beyond the rigid elements. The support surface at the fixation end of the rigid elements (34) can be oriented towards the clamps (20), as shown in FIGS. 10(A to C) or towards another interior surface of the conduit inside the implants (2) as shown on FIGS. 11(A to C).

Figure 12A:
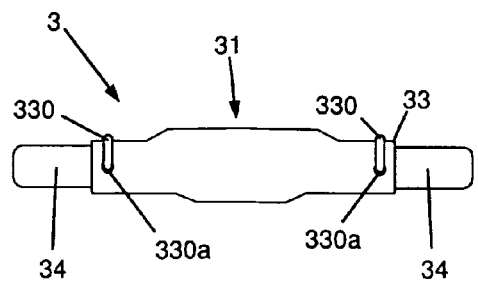
FIGS. 12A and 12B show, respectively, an elevation view and a longitudinal cross sectional view of an embodiment of a linking element that can be used in various embodiments of a vertebral support device according to the invention, the linking element comprising rigid elements disposed within the longitudinal elastic portions.
Figure 12B:
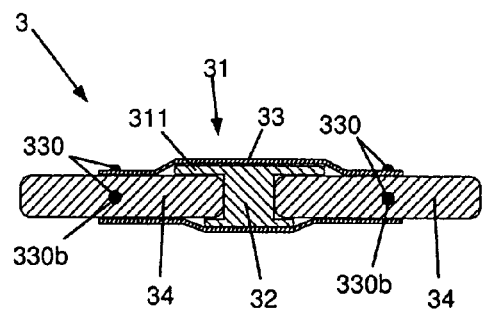
Figure 12C:
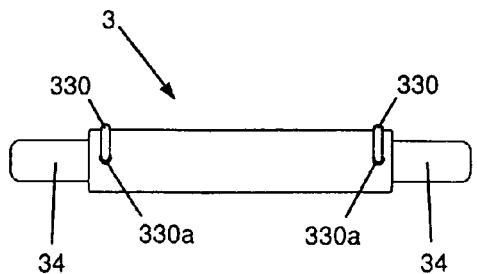
FIGS. 12C and 12D show, respectively, an elevation view and a longitudinal cross sectional view of another embodiment of a linking element that can be used in various embodiments of a vertebral support device according to the invention, in which the rigid elements are disposed within the longitudinal elastic portion.
Figure 12D:
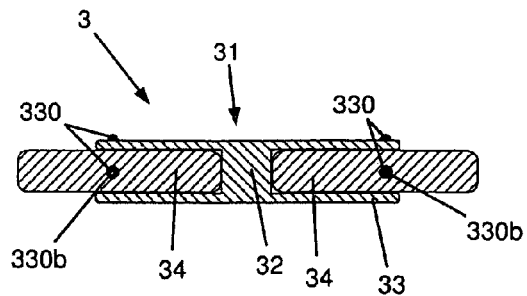

In some embodiments, the longitudinal portion (33) can comprise a kind of sheath (or sleeve) in which the rigid elements (34) are inserted, at least partially. In these embodiments, the rigid elements can comprise solid bars, which have less risk of damaging or impairing the central portion (32) than do hollow tubes. The central (32) and longitudinal (33) portions can be realized in two separated elements, as shown in FIGS. 12A and 12B. In the illustrated embodiments, the longitudinal portion (33) covers both the central portion (32) and, at least partially, the rigid elements (34). The fixation of this longitudinal portion (33) on the rigid elements (34) by the fasteners (330, 331) ensures the cohesion of the ensemble. The central portion (32) can be attached to the rigid elements in various embodiments. In other embodiments, the central (32) and longitudinal (33) portions can be unitary, as shown in FIGS. 12C and 12D. The rigid elements (34) and the central portion (32) can also be attached to each other or not.

Figure 13A:
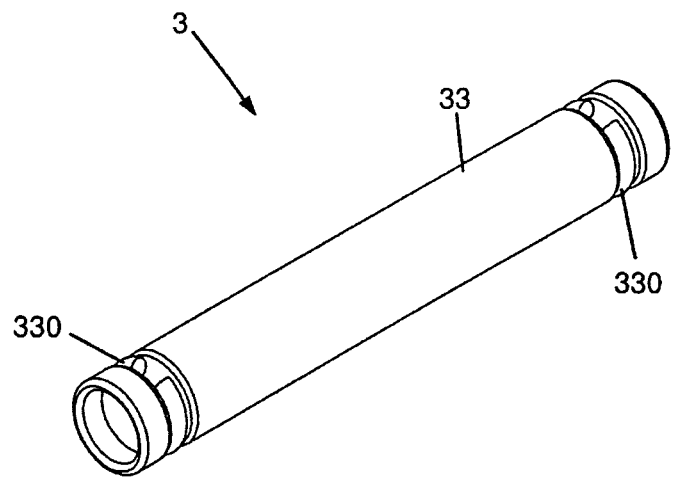
FIGS. 13A and 13B show, respectively, a perspective view and a longitudinal cross sectional view of an embodiment of linking element that can be used in various embodiments of a vertebral support device according to the invention, the linking element comprising rigid elements disposed within the longitudinal elastic portion.
Figure 13B:
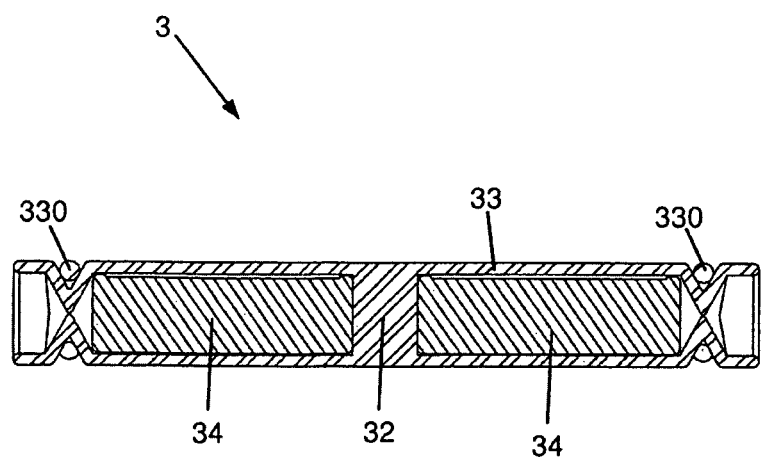
Figure 15A:
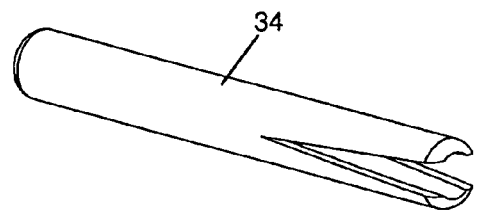
FIG. 15A shows a perspective view of an optional embodiment of rigid element for a linking element that can be used in various embodiments of a vertebral support device according to the invention, the rigid element comprising a longitudinal slit allowing the compression of the longitudinal portion when a fastener is tightened.
Figure 15B:
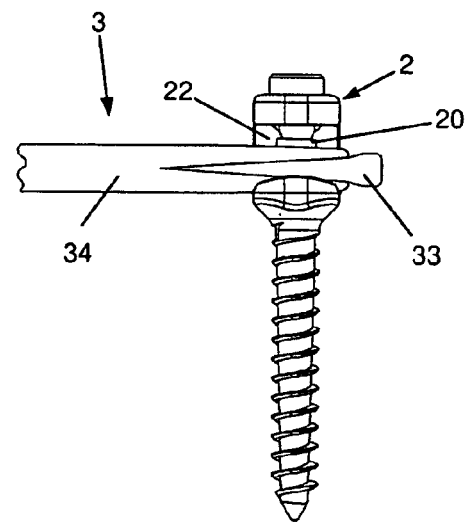
FIGS. 15B and 15C show, respectively, an elevation view and a longitudinal cross sectional view, of part of a vertebral support device comprising an embodiment of a linking element according to FIG. 15A.
Figure 15C:
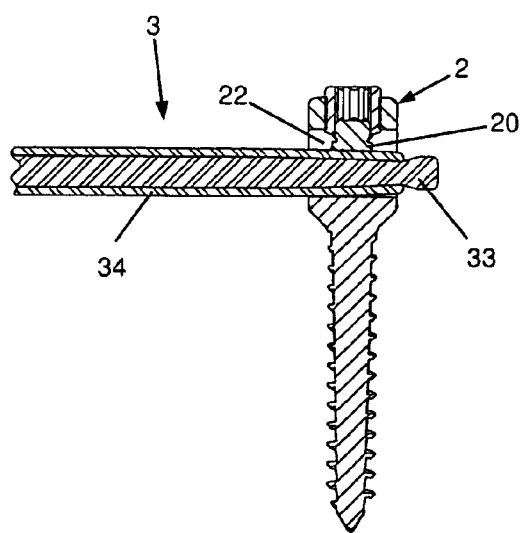

FIGS. 12(A to D) show the fixation of the longitudinal portion (33) on the bars (34), for example, by a removable fastener (330) comprising a wire or filament passing through the bars (34) and the longitudinal portion (33), similarly to the embodiments described previously in reference to FIGS. 8D and 8E. Other embodiments can be adapted to receive any other type of fastener (330, 331), removable or not. Preferably, the longitudinal portion is in tension at rest. In these embodiments of FIGS. 12(A to D), the longitudinal portion is shorter than the ensemble of the linking element (3), formed by the rigid elements (34) and the central portion (32), so that the fixation ends of the rigid elements (34) can receive the clamps (20) without interference. FIGS. 12(A to D) thus show non-limitative examples of fixation of the longitudinal portion (33) by removable fasteners (330) passing through the rigid elements (34) and the longitudinal portion (33). In other embodiments, the longitudinal portion (33) can be longer that the ensemble of the linking element (3) and be kept stretched in tension from both sides or extremities of this ensemble by fasteners (330, 331) such as, for example, staples or rings described previously. FIGS. 13A and 13B show a non-limitative example of such embodiment in which the longitudinal portion (33) is fastened by removable fasteners (330) fixed on each side of the ends of the linking element (3). In this example, the sheath formed by the longitudinal portion (33) is stretched beyond the two ends of the ensemble of the linking element (3) formed by the central portion (32) and the rigid elements (34), the two ends of this sheath being compressed by removable fasteners (330) such as, for example, the staples shown on FIGS. 13(A and B). Fasteners (330, 331) can then be fixed at the extremities of the longitudinal portion (33), and at either of the ends of the rigid elements (34) or on both sides of the rigid elements (34). This imposed tension of the longitudinal portion (33) by the fasteners (330, 331) can be established at the factory or the surgical suite, for example by use of tension marks visible on the periphery of the longitudinal portion (33), at the extremities where the fasteners (330, 331) are to be placed. In another embodiment, the longitudinal portion (33) can be stretched directly by the clamps (20) of the implants (2). For example, in an embodiment in which the longitudinal portion (33) is a sheath threaded on the rigid elements (34), as described for example in reference to FIG. 12(A to D) or 13(A and B), this sheath can be maintained in tension directly by the clamps (20) of the implants (2), to the extent that the longitudinal portion (33) is long enough (or can be stretched enough) to extend from one implant (2) to the other. FIGS. 15A, 15B and 15C show another non-limitative example of possible embodiment in which the longitudinal portion is fixed, and thus stretched (maintained in extension) by the clamps (20) of the implants (2). In this example, the longitudinal portion (33) is inserted, as shown in FIGS. 15B and 15C, inside a hollow rigid element (34) comprising a longitudinal slit at least at one of its end, as particularly visible on FIG. 15A. FIGS. 15B and 15C show that the clamps (20) of the implants, when tightened, compress the part of the rigid element (34) comprising the slit, which result in compression of the longitudinal portion (33) and allows to keep it in tension. Staples or rings can be used as fasteners (330, 331), but other alternatives described herein are possible, for example fixing stops at the ends of the longitudinal portion cooperating with recesses on the bars. Alternatively, no dedicated fastener for the longitudinal portion (33) may be required in some embodiments, for example, where the clamps (20) are configured to fix longitudinal portion (33).

The different embodiments presented here are used to illustrate the possible variants of this present invention, and show that the invention can be used in many different embodiments. Certain particularly advantageous embodiments of this present invention allow the tension of the longitudinal portion (33) to be adjusted during the assembly of the device (1). This assembly, of course, can occur in the factory or at the operating table by the surgeon. In the factory, the tension can be measured precisely and, if necessary, be recorded on tension markers disposed on at least one of the ends of the longitudinal portion (33), so that the surgeon is aware of the values of the tensions that he is adjusting. Accordingly, the present invention also concerns a process for preparation of the device (1).

This process can be implemented in the factory before implantation, and the device delivered assembled. Alternatively, this process can be implemented by the surgeon who will receive the device (1) unassembled (at least in part) and who will assemble it with the tension that he wants. Any of the embodiments described herein that accommodate adjustment of the tension of the longitudinal portion (33) can be adapted for use in the process. The process includes the following steps:

placing the central portion (32) between the rigid elements (34);
placing the longitudinal portion (33) in operative relation to the rigid elements (34);
adjusting the tension of the longitudinal portion (33); and
fixing the longitudinal portion (33) in relation to the rigid elements (34).

During the execution of this process, one implementation includes marking at least one tension mark on the longitudinal portion (33) and adjusting the tension of the longitudinal portion (33). Another implementation includes in the step of fixing the longitudinal portion (33) in relation to the rigid elements (34) includes a step of fastening at least one end of the longitudinal portion (33) with one or more fasteners (330, 331). Another implementation includes inserting of at least one removable lock (330) in at least one hole (330a) in the longitudinal portion (33), along an axis that is substantially perpendicular to the longitudinal axis (L). Such hole (330a) can constitutes a tension mark, and another implementation includes using such a tension mark to determine the tension of the longitudinal portion (33), with another implementation including fixing disposing the fastener (330, 331) in a corresponding hole (or drilling) (330b) in the walls of the hollow tube (34). Such fixing by inserting a removable lock (330) inside at least one hole (330a) present in the longitudinal portion (33), and in a hole (330b) (or drilling) in the walls of the tube (34), optionally can be implemented by the insertion of a wire (330) through these holes and the tying of the wire, for example by the surgeon during the implantation of the device (1).

In another implementation for devices (1) having rigid elements (34) that comprise solid bars equipped with a groove, channel, or chute, placement of the longitudinal portion (33) in operative relation to the rigid elements (34) further comprises inserting the longitudinal portion (33) inside the groove, channel, or chute of the rigid elements (34). As in the embodiment of FIGS. 10(A to C), this step of inserting the longitudinal portion (33) inside the groove, channel, or chute can be associated with a step of inserting the longitudinal portion (33) inside a hole extending the groove, channel, or chute at the fixation end of the rigid elements (34) at the level of the clamps (20) connecting the implants and the linking element. In the embodiments where the rigid elements comprise hollow tubes, the step of placement of the longitudinal portion (33) in operative relation to the rigid elements (34) further comprises a step of inserting the longitudinal portion (33) inside the conduit of the rigid elements (34) and inside a conduit of the central potion (32). In these implementations, placement of the longitudinal portion (33) in operative relation to the rigid elements (34) can further comprise a step of fixing, at the end of the longitudinal portion (33) opposite an end comprising a removable fasteners (330), a fixing stop (331) having an external diameter greater to the diameter of the hollow tubes (34). In another implementation, placement of the longitudinal portion (33) in operative relation to the rigid elements (34) further comprises inserting rigid elements (34) comprising solid bars and the central portion (32) inside a longitudinal portion (33) comprising an elastic sheath or sleeve.

Various steps of the various methods can be implemented before the implantation of the device on the vertebrae. These steps may then constitute at least part of a method for assembling the device prior to implantation. Alternatively, these steps constitute at least part of various methods for implanting the device. During the implantation, the surgeon implementing such a method can perform a step of adjustment of the position, along the longitudinal axis (L), of the rigid elements

(34) with respect to the implants (2), followed by a step of blocking the rigid elements (34) at the desired position by the clamps (20). The implantation of implants on the vertebrae and the adjustment of the orientation of a rigid element in relation to the axis of the spinal column, using polyaxial implants, are described in detail in the applications WO03/049629 and WO2005020829. The steps for implanting the implants (2) by screwing the threaded portion (21) in the vertebral pedicles or by anchoring the hooks (21) into suitable shapes on the vertebrae or recesses made especially in the vertebrae thus do not have to be detailed here. In many implantation procedures, it may be preferable to anchor the implants (2) in the vertebrae without damaging the articular processes (AP). Indeed, various embodiments of the present device (1) are intended to relieve the intervertebral disc while leaving the adjacent vertebrae with a freedom of movement rather than inducing an arthrodesis. Accordingly, in many procedures it may be preferable to leave the articular processes (AP) intact and to avoid their fusion. Thus, during the implantation of bony anchorage implants (2) in the vertebrae (for example, in the vertebral pedicles), the surgeon may take measures to anchor the implants (2) in the vertebrae without damaging the articular processes (AP).

In addition, the centering of the dampening element (31) with respect to the vertebrae can be varied during the implantation. As particularly visible in the non-limitative examples of FIGS. 20 and 21, the implants are anchored at the level of the pedicles of two adjacent vertebrae. The dampening element (31) can then be centered with respect to the articular processes (AP) between these two vertebrae, as particularly visible on FIG. 20, or can be centered with respect to the intervertebral space (IV), as particularly visible on FIG. 21. This centering is performed by the surgeon when fixing the rigid elements (34) in operative relation to the implants (2), by adjusting the position of the rigid elements (34) with respect to the implants (2), along the longitudinal axis (L). This step can also be associated with a step of selecting different rigid elements (34) having a length adapted to the centering position chosen. During the implantation, the surgeon can also adjust the spacing between the vertebrae, for example thanks to a known tool such as forceps. The device according the present invention then will allow this spacing to be maintained while leaving a freedom of movement to the patient.

When the surgeon has implanted the implants on the vertebrae, placed the rigid elements with respect to the implants, and adjusted the tension of the longitudinal portion, the surgeon may elect to clamp only one of the rigid elements (34) with respect to one of the implants (2), and then to adjust the spacing between the vertebrae before clamping the second rigid element (34) with respect to the second implant (2). The method of implantation may thus comprise steps of fixing one of the rigid elements (34) with respect to one of the implants (2) with a clamp (20), centering the dampening element (31) with respect to the vertebrae, spreading the vertebrae apart (for example, using spreading forceps known in the field), and fixing the second rigid element (34) with a clamp (20) to maintain the desired spacing between the vertebrae. The clamps (20), as mentioned previously, comprise tightening means which, in any of the embodiments in which the clamps (20) are on implants (2) comprising a longitudinal channel, allow the rigid elements (34) to be inserted and maintained in the head of the implants (2) without being blocked initially, and then allow blocking them once their position is adjusted. The step of adjustment of the spacing between the vertebrae is facilitated by the translation (along the longitudinal axis) of the rigid elements with respect to the clamps and the tightening of the latter.

As mentioned previously, embodiments using polyaxial anchors (2) can provide adjustment of the orientation of the rigid elements (34). Associated methods can comprise a step of adjustment of the orientation of the longitudinal axis (L) of the rigid elements (34) with respect to the axis of the spinal column, followed by a step of fixing the rigid elements (34) in the desired orientation. In some implementations, adjustment of the position of the rigid element and adjustment of its orientation can be realized during the implantation of the device on the vertebrae. As mentioned previously, the step of adjusting the orientation can be followed by fixation at the chosen orientation, but the orientation may be left free or restricted around a chosen position, even after the tightening of the clamps of the implants, and still be within the scope of the invention.

With the benefit of the disclosure above, those of skill in the art will recognize that many of the various features of the different illustrative embodiments presented here can be combined with each other and with other features known in the art without departing from the scope or spirit of the present invention, and that the present invention can include embodiments in many other forms. Consequently, the embodiments described above must be considered illustrative only, and the invention must not be limited to the details provided above.

The invention claimed is:

1. An elongated linking element for connecting first and second osseous anchoring implants, the linking element having a longitudinal axis and first and second ends disposed at opposite ends of the longitudinal axis and comprising:

first and second rigid, elongated support tubes each having a longitudinal axis and each configured and adapted for connection to a respective one of the first and second osseous anchoring implants, with the first support tube having an exterior end and an interior end disposed at opposite ends of the longitudinal axis of the first support tube, with an open cavity extending completely through the first support tube from the exterior end of the first support tube to the interior end of the first support tube, the second support tube having an exterior end and an interior end disposed at opposite ends of the longitudinal axis of the second support tube, with an open cavity extending completely through the second support tube from the exterior end of the second support tube to the interior end of the second support tube, and with the first support tube disposed at the first end of the linking element and the second support tube disposed at the second end of the linking element, with the longitudinal axis of the first support tube, the longitudinal axis of the second support tube, and the longitudinal axis of the linking element aligned in a generally coaxial arrangement with the open cavity of the first support tube generally aligned with the open cavity of the second support tube along the longitudinal axis of the linking element, and with the interior end of the first support tube facing the interior end of the second support tube to form a gap between the first and second support tubes; and a one-piece elastic link for the first and second support tubes, the link having a longitudinal axis oriented generally coaxially with the longitudinal axis of the linking element and comprising a compressible central body section having a central cross-sectional area perpendicular to the longitudinal axis of the link, a first end along the longitudinal axis of the link, and an opposite second end along the longitudinal axis of the link, with the first end of the link having a recess configured and adapted to receive the interior end of the first support tube,

- a first elongated protrusion having a first cross-sectional area perpendicular to the longitudinal axis of the link that is smaller than the central cross-sectional area, the first elongated protrusion extending from the first end of the central body section into and through the open cavity of the first support tube to the exterior end of the first support tube,
- a second elongated protrusion having a second cross-sectional area perpendicular to the longitudinal axis of the link that is smaller than the central cross-sectional area, the second elongated protrusion extending from the second end of the central body section into and through the open cavity of the second support tube to the exterior end of the second support tube, and
- a fixing stop extending the first elongated protrusion past the exterior end of the first support tube and having a third cross-sectional area perpendicular to the longitudinal axis of the link that is larger than the first cross-sectional area, the fixing stop configured and arranged to retain the first elongated protrusion within the first support tube.

2. The linking element of claim 1 in which the central body section is disposed substantially equally distant from the exterior end of the first support tube and the exterior end of the second support tube.

3. The linking element of claim 1 central body section is disposed closer to the exterior end of the first support tube than to the exterior end of the second support tube.

4. The linking element of claim 1 in which the link comprises plural elastic materials.

5. The linking element of claim 1 in which the link comprises at least one elastic weave or braid of synthetic fibers having stitches or plaits, respectively, the tightness of which at least partially affects the elasticity of the link.

6. The linking element of claim 1 in which the second elongated protrusion is adjustably fixed to the second support tube with a link fastener, and in which the second elongated protrusion has a tension adjustable at least in part by the link fastener.

7. The linking element of claim 6 in which the second elongated protrusion has a tension mark identifying a tension of the longitudinal elastic portion.

8. The linking element of claim 1 in which the central body section and the first and second elongated protrusions are each comprised of a unitary weave or braid of synthetic fibers having uniform elastic properties through the central body section and the first and second elongated protrusions.

9. The linking element of claim 1 in which the central body section and the first and second elongated protrusions each are comprised of a unitary weave or braid of synthetic fibers having different elastic properties through the central body section and through the first and second elongated protrusions.

10. The linking element of claim 1 in which the link comprises a bending stop.

11. The linking element of claim 10 in which the bending stop comprises an elastic material.

12. The linking element of claim 1 in which at least one of the first and second support tubes has a flat exterior surface disposed parallel to the longitudinal axis.

13. The linking element of claim 6 in which the second elongated protrusion comprises a hole setting a tension mark and the link fastener comprises a removable lock fitting the hole and determining the tension of the longitudinal elastic portion.

* * * * *